United States Patent [19]

Campbell, Jr. et al.

[11] Patent Number: 4,546,104
[45] Date of Patent: Oct. 8, 1985

[54] PYRAZOLOPYRIDINE CYCLOALKANONES AND PROCESS FOR THEIR PREPARATION

[75] Inventors: James B. Campbell, Jr., Malvern; Thomas M. Bare, West Chester, both of Pa.

[73] Assignee: ICI Americas Inc., Wilmington, Del.

[21] Appl. No.: 659,615

[22] Filed: Oct. 11, 1984

[30] Foreign Application Priority Data

Nov. 4, 1983 [GB] United Kingdom ......................... 8329531

[51] Int. Cl.[4] .................. C07D 471/04; C07D 231/38; A61K 31/47
[52] U.S. Cl. ..................................... 514/293; 546/82; 546/15; 548/362
[58] Field of Search ..................... 546/82, 15; 548/362; 424/256, 258

[56] References Cited

U.S. PATENT DOCUMENTS 4,018,779 4/1977 Hoehn .................................. 260/296

FOREIGN PATENT DOCUMENTS 1445719 1/1969 Fed. Rep. of Germany ........ 546/82
1355205 6/1974 United Kingdom ................... 546/82

*Primary Examiner*—Henry R. Jiles
*Assistant Examiner*—Barbara Cassatt
*Attorney, Agent, or Firm*—Rosemary M. Miano

[57] ABSTRACT

Novel tetrahydropyrazolo-[3,4-b]quinolinones, cyclopenta[b]pyrazolo-[4,3-e]pyridinones and cyclohepta[b]-pyrazolo[4,3-e]pyridinones, useful as anxiolytics having reduced side effects, are disclosed, including methods of preparation, pharmaceutical compositions containing them and intermediates used in their preparation.

12 Claims, No Drawings

PYRAZOLOPYRIDINE CYCLOALKANONES AND PROCESS FOR THEIR PREPARATION

BACKGROUND OF THE INVENTION

The present invention comprises certain pyrazolopyridine cycloalkanones, their use as central nervous system depressants, methods for their preparation, pharmaceutical compositions containing them and intermediates used in their preparation.

U.S. Pat. No. 4,018,779 discloses certain tetracyclic pyrazolopyridine compounds, i.e., derivatives of 10,11-dihydrobenzo[4,5]cyclohepta[1,2-b]pyrazolo-[4,3-e]-pyridin-5(1H)-ones and salts thereof, which are stated to be useful for the relief of anxiety and tension.

SUMMARY OF THE INVENTION

The compounds of the invention are tetrahydropyrazolo-[3,4-b]quinolinones, cyclopenta[b]pyrazolo[4,3-e]pyridinones, and cyclohepta[b]pyrazolo[4,3-e]pyridinones. These compounds have been found to possess potent anxiolytic activity in animals with reduced side effects and are useful for such purposes. For example, they are less sedating and show a lower propensity to potentiate alcohol at effective anxiolytic doses compared to known anxiolytics such as diazepam. Also part of the invention are pharmaceutical compositions containing one or more of the compounds for administration to an animal in need of an anxiety-reducing medication, such a method of treatment, methods for the synthesis of the compounds as well as novel intermediates used in the syntheses.

DETAILED DESCRIPTION OF THE INVENTION

The compounds of the invention are tricyclics of the following formula (I):

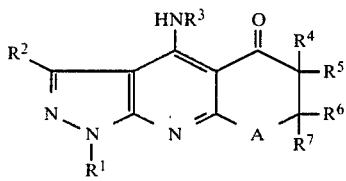

wherein

A is a direct link or a divalent radical having the formula $(CR^8R^9)_n$;

n is 1 or 2;

$R^1$ is hydrogen; an alkyl of 1 to 10 carbons optionally substituted independently by a member selected from a group consisting of hydroxy, cyano, oxo and alkoxy having 1 to 6 carbons, or one to three member(s) selected from a group consisting of halogen, an alkyl having 1 to 6 carbons, and an alkyl substituted by 1 to 3 halogens; a cycloalkyl of 3 to 8 carbons; a cycloalkylalkyl of 4 to 12 carbons; an alkenyl or alkynyl of 2 to 10 carbons, optionally substituted independently by 1 to 3 member(s) selected from a group consisting of halogen and an alkyl of 1 to 6 carbons; an aryl of 6 to 10 carbons optionally substituted independently by one or two member(s) selected from a group consisting of halogen, hydroxy, an alkyl of 1 to 6 carbons, an alkyl of 1 to 6 carbons substituted by one or more fluoros, and an alkoxy of about 1 to 6 carbons; an arylalkyl having 6 to 10 carbons in the aryl and 1 to 4 carbons in the alkyl, wherein said aryl portion may optionally be substituted independently by 1 or 2 member(s) selected from a group consisting of halogen, hydroxy, an alkyl of 1 to 6 carbons, an alkyl of 1 to 6 carbons substituted by one or more fluoros, and an alkoxy of 1 to 6 carbons;

$R^2$ is hydrogen; or an alkyl of 1 to 6 carbons;

$R^3$ is hydrogen; an alkyl of 1 to 6 carbons optionally substituted by a member selected from a group consisting of hydroxy and oxo; an alkanoyl of 2 to 6 carbons; or an aroyl of 6 to 10 carbons;

$R^4$ and $R^5$, may be the same or different and are each hydrogen; an alkyl of 1 to 10 carbons optionally substituted independently by one or two member(s) selected from a group consisting of hydroxy, oxo, alkoxy of 1 to 6 carbons, an alkyl of 1 to 6 carbons, and a halogenoalkyl having 1 to 6 carbons and 1 to 3 halogens; a cycloalkyl of 3 to 8 carbons; a cycloalkylalkyl of 4 to 10 carbons; an alkenyl or alkynyl of 3 to 10 carbons optionally substituted independently by 1 to 3 member(s) selected from a group consisting of an alkyl of 1 to 6 carbons and halogen; a cycloalkenyl of 4 to 8 carbons optionally substituted independently by 1 or 2 member(s) selected from a group consisting of halogen and an alkyl having 1 to 6 carbons; a cycloalkenylalkyl wherein the cycloalkenyl portion has 4 to 8 carbons and the alkyl portion has 1 to 3 carbons, optionally substituted independently in the cycloalkenyl portion by 1 or 2 member(s) selected from a group consisting of an alkyl of 1 to 6 carbons (e.g., a 2 member substitution may include two methyls or a methyl and an ethyl); an aryl of 6 to 10 carbons optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, amino and a halogenoalkyl having 1 to 6 carbons and 1 to 3 of halogen; an arylalkyl having 6 to 10 carbons in the aryl portion and 1 to 4 carbons in the alkyl wherein the aryl portion is optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, an amino and a halogenoalkyl having 1 to 6 carbons and 1 to 3 of halogen; an alkanoyl of 1 to 6 carbons; or an aryl (oxo-substituted)alkyl of 7 to 12 carbons; or, when taken together with the carbon atom to which they are attached, $R^4$ and $R^5$ may be selected to form a spiro ring having from 4 to 7 carbons wherein said spiro ring may optionally be substituted by a member selected from a group consisting of an alkyl having 1 to 6 carbons and an alkenyl having 2 to 6 carbons;

$R^6$, $R^7$, $R^8$ and $R^9$ may be the same or different and are each hydrogen; an alkyl of 1 to 6 carbons; or an alkenyl of 2 to 6 carbons;

and a pharmaceutically acceptable salt thereof.

Unless otherwise specified the alkyls, alkenyls and alkynyls described for this invention may be straight or branched chain. Substitutions are taken independently of each other; thus, a three member substitution from a listed group may include three different members, two of the same members or all identical members. The term halogen includes fluorine, chlorine, bromine and iodine.

The above definitions shall apply throughout this specification except where specifically indicated otherwise.

$R^1$, in particular, is hydrogen; an alkyl of 2 to 7 carbons, especially a straight chain alkyl, more preferably of 2 to 5 carbons, optionally substituted by a member selected from a group consisting of hydroxy, oxo, an alkyl of 1 to 6 carbons, and a halogenoalkyl wherein the halogenoalkyl is optionally substituted by 1 to 3 of chloro or fluoro; a cycloalkyl of 4 to 8 carbons; a cycloalkylalkyl of 4 to 12 carbons, more preferably 4 to 10 carbons; an alkenyl or alkynyl of 2 to 7 carbons, more preferably 2 to 6 carbons, and most preferably 2 to 6 carbons wherein the double or triple bond is on the terminal carbon or on one carbon removed from the terminal carbon (the alkenyl or alkynyl may also be optionally substituted independently by 1 to 3 member(s) of a group consisting of halogen and an alkyl of 1 to 6 carbons, (e.g., 3 fluoros, 2 chloros and a methyl, 2 methyls) or more preferably by a halogen or an alkyl of 1 to 4 carbons); an aryl of 6 to 10 carbons, more preferably phenyl, optionally substituted independently by one or two member(s) selected from a group consisting of halogen, hydroxy, an alkyl of 1 to 6 carbons, and an alkyl of 1 to 6 carbons substituted by one or more fluoro, particularly phenyl substituted by 1 or 2 member(s) of a group consisting of halogen, hydroxy, an alkyl of 1 to 4 carbons, trifluoromethyl and methoxy, and more particularly phenyl substituted independently by a member of a group consisting of hydroxy and an alkyl of 1 to 4 carbons, or by 1 or 2 of chloro or fluoro (e.g., one of chloro or fluoro); an arylalkyl having 6 to 10 carbons in the aryl and 1 to 4 carbons in the alkyl, wherein the aryl portion may optionally be substituted by 1 or 2 member(s) selected from a group consisting of halogen, hydroxy, an alkyl of 1 to 6 carbons, an alkoxy of 1 to 6 carbons and an alkyl of 1 to 6 carbons substituted by one or more fluoros, more particularly a phenylalkyl or a (substituted phenyl)alkyl wherein the alkyl is 1 to 4 carbons and the substitution is 1 or 2 member(s) selected from a group consisting of halogen, hydroxy, an alkyl of 1 to 4 carbons, trifluoromethyl and methoxy, e.g., benzyl optionally substituted by a member of a group consisting of chloro, fluoro and an alkyl of 1 to 4 carbons;

$R^2$, in particular, is hydrogen;

$R^3$, in particular, is hydrogen; an alkyl of 1 to 6 carbons, more particularly 1 to 4 carbons, optionally substituted by hydroxy or oxo; an alkanoyl of 2 to 4 carbons, e.g., acetyl, propanoyl or butanoyl; or a benzoyl;

$R^4$ and $R^5$, in particular, are the same or different and are each hydrogen; an alkyl of 1 to 6 carbons, especially 1 to 5 carbons, optionally substituted by a member selected from the group consisting of hydroxy, oxo, an alkoxy of 1 to 6 carbons, an alkyl of 1 to 6 carbons and a halogenoalkyl having 1 to 6 carbons, especially 1 to 4 carbons, and 1 to 3 halogens, especially chloro or fluoro; a cycloalkyl of 4 to 8 carbons; a cycloalkylalkyl of 4 to 10 carbons; an alkenyl or alkynyl of 3 to 6 carbons optionally substituted by 1 to 3 of a halogen, especially 1 or 2 of chloro, or an alkyl of 1 to 6 carbons, especially 1 to 4 carbons, and more particularly 1 to 2 of methyl, and more preferably where a double or triple bond is terminal or one carbon removed from the terminal carbon of the alkenyl or alkynyl; a cycloalkenyl of 4 to 8 carbons, especially 5 to 8 carbons, optionally substituted by 1 or 2 member(s) selected from a group consisting of halogen and an alkyl having 1 to 6 carbons; a cycloalkenylalkyl wherein the cycloalkenyl portion has 4 to 8 carbons and the alkyl portion has 1 to 3 carbons, optionally substituted in the cycloalkenyl portion by 1 or 2 of an alkyl of 1 to 6 carbons; an aryl of 6 to 10 carbons, more particularly phenyl, optionally substituted independently by a member selected from a group consisting of nitro, cyano, an alkoxycarbonyl of 2 to 7 carbons, and a mono or dialkyl-substituted amino of 1 to 6 carbons, especially 1 to 4 carbons, in each alkyl, or by 1 or 2 member(s) selected from a group consisting of halogen (especially chloro or fluoro), hydroxy, an alkyl or 1 to 6 carbons (especially 1 to 4 carbons), an alkanoyl of 1 to 6 carbons, an alkoxy of 1 to 6 carbons, amino, and a halogenoalkyl having 1 to 6 carbons and 1 to 3 of halogen; or an arylalkyl having 6 to 10 carbons in the aryl portion, e.g., phenyl, and 1 to 4 carbons in the alkyl portion wherein the aryl portion is optionally substituted by a member selected from a group consisting of cyano, alkoxy carbonyl of 2 to 7 carbons, a mono or dialkyl-substituted amino of 1 to 4 carbons in each alkyl, or by 1 or 2 member(s) selected from a group consisting of halogen, hydroxy, an alkyl of 1 to 6 carbons (especially 1 to 4 carbons), an alkanoyl of 1 to 6 carbons, an alkoxy of 1 to 6 carbons (especially 1 to 4 carbons), a halogenoalkyl having 1 to 3 halogen and 1 to 6 carbons (especially 1 to 4 carbons), and an alkanoyl of 1 to 6 carbons, e.g., phenylacetyl or benzoyl; or when taken together with the carbon to which they are attached, $R^4$ and $R^5$ may be selected to form a spiro ring which has from 4 to 6 carbons, and which may optionally be substituted by a member selected from a group consisting of an alkyl having 1 to 6 carbons and an alkenyl having 2 to 6 carbons;

$R^6$, $R^7$, $R^8$ and $R^9$ may be the same or different and in particular are each hydrogen; an alkyl of 1 to 4 carbons, e.g., methyl, ethyl, propyl, butyl; 2-propenyl; or 3-butenyl.

A and n, in particular, are as defined above.

The pharmaceutically acceptable salts of the compounds of formula (I) are, for example, physiologically acceptable acid-addition salts such as mineral acid salts, e.g., hydrohalides, especially hydrochlorides and hydrobromides, sulfates, nitrates and phosphates, or organic acid salts, e.g., methanesulfonates.

Compounds of formula (I) and intermediates may exist in the form of optical isomers, e.g., where $R^6$ is alkyl and $R^7$ is hydrogen or when an alkyl group is not symmetric such as 1-methyl-1-butyl, and geometric isomers, e.g., the cis and trans alkenyl groups. The present invention comprises all such optical and geometric isomers and racemates. These intermediates are useful in pharmacological testing.

Preferred compounds of the formula (I) are 4-amino-1-pentyl-6-(2-propenyl)-5H-1,6,7,8-tetrahydropyrazolo[3,4-b]quinolin-5-one ($R^1$=pentyl, $R^4$=2-propenyl, $R^2=R^3=R^5=R^6=R^7=R^8=R^9$=H, n=1; illustrated in Example 12d); 4-amino-6,7-dihydro-1-pentyl-6-propylcyclopenta[b]pyrazolo[4,3-e]pyridin-5(1H)-one ($R^1$=pentyl, $R^4$=propyl, $R^2=R^3=R^5=R^6=R^7$=H, A=a direct link; illustrated in Example 14d); 4-amino-6,7-dihydro-1-pentyl-6-(2-propenyl)cyclopenta[b]pyrazolo[4,3-e]pyridin-5(1H)-one ($R^1$=pentyl, $R^4$=2-propenyl, $R^2=R^3=R^5=R^6=R^7$=H, A=a direct link; illustrated in Example 15d); 4-amino-6,7-dihydro-1-(4-pentynyl)-6-(2-propenyl)cyclopenta[b]pyrazolo[4,3-e]pyridin-5(1H)-one ($R^1$=4-pentynyl, $R^2=R^3=R^5=R^6=R^7$=H, $R^4$=2-propenyl, A=a direct link; illustrated in Example 26c); 4-amino-1-(3-pentynyl)-6-(2-propenyl)-5H-1,6,7,8-tetrahydropyrazolo[3,4-b]quinolin-5-one ($R^1$=3-pentynyl, $R^2$=$R^3$=$R^5$=$R^6$=$R^7$=$R^8$=$R^9$=H, $R^4$=2-propenyl, n=1 illustrated in Example 36); 4-amino-1-(4-pentynyl)-6-(2-propenyl)-5H-1,6,7,8-tetrahydropyrazolo[3,4-b]quinolin-5-one ($R^1$=4-pentynyl, $R^2$=$R^3$=$R^5$=$R^6$=$R^7$=$R^8$=$R^9$=H, $R^4$=2-propenyl, n=1; illustrated in Example 37); 4-amino-6-(3,3-dichloro-2-propenyl)-1-(4-pentynyl)-5H-1,6,7,8-tetrahydropyrazolo[3,4-b]quinolin-5-one ($R^1$=4-pentynyl, $R^2$=$R^3$=$R^5$=$R^6$=$R^7$=$R^8$=$R^9$=H, $R^4$=3,3-dichloro-2-propenyl, n=1; illustrated in Example 39); and pharmaceutically acceptable acid-addition salts thereof.

Particularly preferred compounds of the formula (I) are 4-amino-6,7-dihydro-1-pentyl-6-(2-propenyl)cyclopenta[b]pyrazolo[4,3-e]pyridin-5(1H)-one and pharmaceutically acceptable acid-addition salts thereof.

Compounds of the invention having formula I may be prepared by condensing an aminocyanopyrazole of the following formula (II)

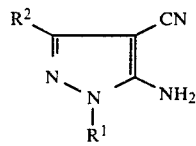

with a cycloaliphatic diketone of the following formula (III)

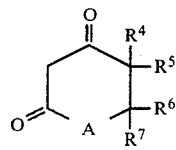

to yield an enamine of the formula (IV)

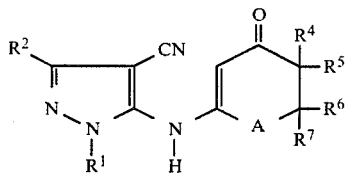

where A, $R^1$, $R^2$, $R^4$, $R^5$, $R^6$, and $R^7$ are as previously defined. (Compounds of the formula III exist as equilibrium mixtures of the keto and the enol forms, as is recognized by those skilled in the art. Only the keto forms are shown). As previously noted, A=a direct link or $(CR^8R^9)_n$ where n=1 or 2 and $R^8$ and $R^9$ are each hydrogen, alkyl, or alkenyl as defined above. Where n=2, the two groups $R^8$ and the two groups $R^9$ may be chosen independently of each other. The condensation reaction may take place at about 75° to 150° C. with loss of water in a solvent such as toluene with an enamine promoter such as p-toluenesulfonic acid.

When the starting diketone (III) is symmetrical (i.e., symmetrical about an axis drawn through the C2 carbon atom), a single enamine of the formula (IV) is obtained. When an unsymmetrical diketone (III) is used, a mixture of enamines (IV) is obtained and separation is necessary.

The compound of formula (IV) undergoes internal cyclization when heated in the presence of an appropriate Lewis acid catalyst such as zinc chloride or copper (I) acetate, resulting in a compound of the formula (I) in which $R^3$ is hydrogen. Copper acetate is preferred because it makes possible the use of lower cyclization temperatures. (Cyclization may be carried out 120° C. in the presence of copper (I) acetate, vs. about 180° C. in the presence of zinc chloride).

An alternate and more preferred method of inducing cyclization of compounds of formula (IV) wherein A is not a direct link comprises the use of trimethylaluminum as a catalyst at temperatures from ambient to 70° C.

A preferred method of inducing cyclization of compounds of formula (IV) wherein A is a direct link comprises the use of sodium hydride with subsequent addition of cadmium chloride. The temperatures used may range from about 70° C. to about 150° C., e.g., 110° C.

Compounds of the formula (I) in which $R^3$ is other than hydrogen can be obtained by reacting the corresponding compound (I) where $R^3$ is hydrogen, with a halide of the general formula $R^{13}X$ where $R^{13}$ is as previously defined for $R^3$, excluding hydrogen, and X is a halogen, in a basic medium.

Compounds of the formula (I) in which $R^1$ may contain a sensitive functionality which may be adversely affected by cyclization conditions may be formed in an alternate manner. 1-(2-Hydroxyethyl)-5-amino-4-cyanopyrazole, prepared from hydroxyethylhydrazine and ethoxymethylenemalononitrile as described below, was converted to 1-(2-chloroethyl)-5-amino-4-cyanopyrazole. Condensation with the appropriate diketone where A is not a direct link affords enamines of the formula (IV) with $R^1$=2-chloroethyl and $R^2$, $R^4$, $R^5$, $R^6$, $R^7$, $R^8$, $R^9$ are as previously defined. Cyclization with trimethylaluminum affords compounds of the formula (I) with $R^1$=2-chloroethyl. Dehydrohalogenation using 1,8-diazabicyclo[5.4.0]undec-7-ene and subsequent acid catalyzed hydrolysis of the intermediate according to the procedure of Muchowski et al., *Can. J. Chem.*, Vol. 61, 1697–1702 (1983) gives the unsubstituted compound of the formula (I) with $R^1$=H. Reaction with the appropriate alkyl halide in the presence of a base (e.g., potassium carbonate) then yields compounds of the formula (I) where $R^1$, is not hydrogen and is as defined previously.

The aminocyanopyrazole starting materials of formula (II) can be prepared by reacting a hydrazine of the formula $R^1$-NH-NH$_2$ (V) with an alkoxymethylenemalononitrile of the following formula (VI)

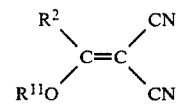

where $R^{11}$ is a lower alkyl radical (e.g., 1 to 6 carbons), preferably ethyl, and $R^1$ and $R^2$ are as previously defined, at about 40° to 80° C. in a solvent such as an alcohol, e.g., ethanol. The synthesis of such 4-cyanopyrazoles is described in U.S. Pat. No. 3,732,225.

Pyrazoles of the formula (II) may also be formed by reaction of 4-cyano-3-aminopyrazole (Formula II, $R^1$=$R^2$=H) with an alkyl halide in the presence of a base. The resulting mixture contains the desired pyrazole of the formula (II) with $R^1$ not hydrogen and $R^2$ as defined previously and a 1-alkyl-3-amino-4- cyanopyrazole. Separation of the isomeric pyrazoles affords the desired compounds.

1,3-Cyclopentanedione and 1,3-cyclohexanedione, both of which are starting materials of formula (III), are commercially available. Also, these and other cycloaliphatic 1,3-diketones of formula (III) can be made according to known methods.

According to a first method, 1,3-cyclohexanediones of formula (III) where $R^4$ and $R^5$ are hydrogen, and A is the methylene radical (i.e., $R^8$ and $R^9$ are hydrogen and n=1), can be prepared by condensing an aliphatic ketone of the following formula (VII)

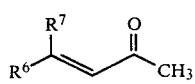
VII with a malonic ester of the following formula (VIII)

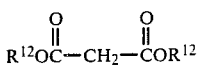
VIII when $R^{12}$ is alkyl, preferably lower alkyl (1 to 6 carbons), most preferably methyl, to give a 4-carboalkoxy (e.g., 4-carbomethoxy) derivative of a compound of the following formula (III-A),

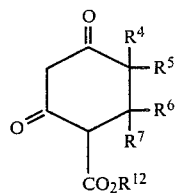
III-A which on hydroysis and decarboxylation yields the corresponding compound of the formula (III) when $R^4$ and $R^5$ are hydrogen and A=CH$_2$ (i.e., $R^8$ and $R^9$ are hydrogen and n=1). The above method is particularly suitable for preparing substituted 1,3-cyclohexanediones where either $R^6$ or $R^7$ or both is other than hydrogen (but otherwise both are as previously defined), although it can also be used for preparing 1,3-cyclohexanedione.

Aliphatic ketones of the formula (VII) can be prepared by known methods, e.g., by reacting an aliphatic aldehyde with acetonyl diethyl phosphonate according to the method of J. K. Crandall et al., *Journal of Organic Chemistry*, Vol. 35, no. 9, pp. 3049–3053 (1970), or by reacting a saturated aliphatic aldehyde with acetone at elevated temperature in the presence of a base or acid catalyst. The malonic esters (VIII) are either known or capable of being prepared by known methods.

A variation of this method can be used when a 6-substituted 1,3-cyclohexanedione (i.e., a compound of the formula III where $R^4$ is other than hydrogen) is desired. According to this variation, an aliphatic ketone of the formula (VII) is reacted with a substituted malonic ester of the following formula (VIII-A)

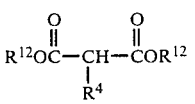
VIII-A where $R^4$ and $R^{12}$ are as previously defined. The resulting 4-carboalkoxy diketone after hydrolysis and decarboxylation yields a 1,3-cycloalkanedione of the formula III where $R^4$ is a substituent other than hydrogen (but otherwise as previously defined), $R^5$, $R^8$ and $R^9$ are hydrogen, and n=1.

According to a second general method, a 2-cycloalkenone, either substituted or not, of 5, 6 or 7 nuclear carbon atoms (e.g., 2-cyclopentenone, 2-cyclohexenone or 2-cycloheptenone) is reacted with hydrogen peroxide under alkaline conditions according to the method described in *Organic Synthesis*, Collective Volume IV, pp. 552–553 (1963), and the resulting 2,3-epoxycycloalkanone is converted to the corresponding 1,3-cycloalkanedione of the formula III according to the method disclosed in *Journal of the American Chemical Society*, Vol. 102, no. 6, pp. 2095–2096 (1980). Among the 1,3-cycloalkanediones which the authors disclose as being prepared in this manner are 1,3-cyclopentanedione, 1,3-cyclohexanedione and 1,3-cycloheptanedione.

A third general method (including variations thereon) is useful for alkylating unsubstituted or partially substituted cycloaliphatic 1,3-diketones of the formula (III) in order to produce compounds of the formula (III) in which one or more of the substituents $R^4$ and $R^5$ is other than hydrogen. According to this third method, a 1,3-cycloalkanedione of the formula (III) in which at least one of $R^4$ and $R^5$ is hydrogen, is reacted with a lower aliphatic alcohol, e.g., ethanol or 2-methyl-1-propanol (isobutanol), giving an intermediate of the following formula (IX)

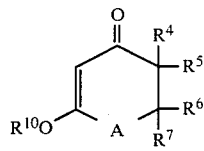
IX where $R^{10}$ is lower alkyl (e.g., 1 to 6 carbons), at least one of $R^4$ and $R^5$ is hydrogen, and A is as previously defined. (Also, 3-ethoxy-2-cyclohexenone, which is a compound of the formula IX, is commercially available). This intermediate may be dissolved in a suitable solvent (e.g., tetrahydrofuran) and added to chilled ($-100°$ to $-50°$ C., e.g., $-78°$ C.) freshly prepared lithium diisopropylamide (which may be prepared by adding a lithium alkyl in an inert solvent to a solution of diisopropylamine in a suitable solvent at 0° C. and cooling the resulting lithium diisopropylamide solution to $-78°$ C.). Equimolar quantities of the intermediate (IX) and lithium diisopropylamide, or a slight excess of the latter, are used. Reaction of the ketone (IX) with lithium diisopropylamide gives a solution of the enolate ion corresponding to the ketone. A compound of the formula $R^4X$ where X is a halogen, preferably an iodoalkane of the formula $R^4I$ where $R^4$ is alkyl (for example, iodomethane or iodoethane), is added to the cold enolate ion solution and reaction is allowed to warm to and proceed at ambient temperature. An excess of the compound $R^4X$ is ordinarily used. This gives a second intermediate of the formula (IX) where one of the groups $R^4$ and $R^5$ which was previously hydrogen is now a substituent other than hydrogen. Acid hydrolysis of this intermediate gives a diketone of the formula (III) where $R^4$ and $R^5$ are the same as in the second intermediate.

Substitution takes place preferentially at the position adjacent to the carbonyl group. Thus, when at least one of $R^4$ and $R^5$ in the starting ketone (IX) is hydrogen, $R^4$ ($R^5$ where $R^4$ in the starting ketone (IX) is other than hydrogen) is substituted, and $R^5$ (or $R^4$), $R^6$ and $R^7$ remain the same as in the starting ketone.

By way of specific example, 1,3-cyclohexanedione (formula III where $R^4$, $R^5$, $R^6$ and $R^7$ are hydrogen and A is methylene) may be reacted with ethanol to give 3-ethoxy-2-cyclohexenone (IX). This compound reacts with lithium diisopropylamide followed by iodomethane to give 3-ethoxy-6-methyl-2-cyclohexenone (formula IX where $R^4$ is methyl and $R^5$, $R^6$ and $R^7$ are hydrogen), which upon hydrolysis yields 4-methyl-1,3-cyclohexanedione (formula III where n=1, $R^4$=CH$_3$ and $R^5$=$R^6$=$R^7$=$R^8$=$R^9$=H).

The above general method is well known in the art, see for example, G. Stork et al., *Journal of Organic Chemistry*, Vol. 38, no. 9, pp. 1775–1776 (1973).

Variations on the above general method can be used when it is desired to introduce two substituent groups into a diketone of the formula (III).

To form a disubstituted diketone of the formula (III) in which both substituents are on the same carbon atom, one reacts a diketone (III) in which $R^4$ and $R^5$ are hydrogen according to the foregoing sequence of reactions, obtaining the monosubstituted derivative in which $R^4$ is a substituent other than hydrogen and $R^5$, $R^6$ and $R^7$ remain the same as before. The sequence is then repeated with the monosubstituted derivative as the starting material. This yields a disubstituted 1,3-cycloalkanedione of the formula (III) where $R^4$ and $R^5$ are substituents other than hydrogen and $R^6$ and $R^7$ are the same as in the starting diketones (III). Substitution in this manner takes place preferentially to substitution of hydrogen atoms attached to any other carbon atom.

Compounds of the formula (III) having a spiro ring, i.e., in which $R^4$ and $R^5$ together with the carbon atom to which they are attached form a spiro ring, may be formed by reacting an α,ω-dihaloalkane with the enolate ion corresponding to a 3-alkoxy-2-enone of the formula (IX) and hydrolyzing the resulting intermediate. This method is described in the *Journal of the American Chemical Society*. Vol. 95, pp. 3414–3415 (1973).

Substituents may be introduced on adjacent carbon atoms of a diketone (III) in which A is a direct link, in the manner disclosed by M. Koreeda et al., *Journal of the Chemical Society*, Chemical Communications, pp. 449–450 (1979). The sequence of steps and reaction conditions are as disclosed above for introducing a single substituent, except that approximately 2 (or slightly in excess of 2) mols of lithium diisopropylamide per mol of alkoxy-substituted enone (IX) are required, and the amount of alkylating agent $R^4$X (e.g., iodomethane) is in excess of 2 mols per mol of alkoxy-substituted enone (IX). According to this variation, one starts with a diketone (III) in which $R^4$ and $R^6$ are hydrogen, and one obtains a diketone (III) in which $R^4$ and $R^6$ are alkyl or alkenyl.

The above routes for preparing diketones of the formula (III) may be used either singly or in combination, depending on the desired substituents in the diketone (III) and in the final compound (I).

The compounds of this invention of the formula (I) and their pharmaceutically acceptable salts are useful in the suppression of central nervous system activity in mammals, e.g., in humans, by the suppression of convulsions, the relaxation of skeletal muscles, and particularly for the treatment of anxiety.

The pharmaceutical compositions of the invention may be prepared and used according to methods known for the compounds cartazolate and tracazolate. Specifically, the new compounds of this invention are central nervous system depressants and may be used as tranquilizers or ataractic agents for the relief of anxiety and tension states, for example, in mice, cats, rats, dogs and other mammalian species such as man, in the same manner as chlordiazepoxide. For this purpose a compound or mixture of compounds of formula (I), or non-toxic physiologically acceptable acid addition salts thereof, may be administered orally or parenterally in a conventional dosage form such as tablet, pill, capsule, injectable or the like. The dosage in mg/kg of body weight of compounds of the present invention in mammals will vary according to the size of the animal and particularly with respect to the brain/body weight ratio. In general, a higher mg/kg dosage for a small animal such as a dog will have the same effect as a lower mg/kg dosage in an adult human. A minimum effective dosage for a compound of formula (I) will be at least about 0.1 mg/kg of body weight per day for mammals with a maximum dosage for a small mammal such as a dog, of about 100 mg/kg per day. For humans, a dosage of about 0.1 to 12 mg/kg per day will be effective, e.g., about 5 to 600 mg/day for an average man. The dosage can be given once daily or in divided doses, e.g., 2 to 4 doses daily, and such will depend on the duration and maximum level of activity of a particular compound. The dose may be conventionally formulated in an oral or parenteral dosage form by compounding about 10 to 250 mg per unit of dosage of conventional vehicle, excipient, binder, preservative, stabilizer, flavor or the like as called for by accepted pharmaceutical practice, e.g., as described in U.S. Pat. No. 3,755,340. The compounds of this invention may be used in pharmaceutical compositions comprising a compound of formula I as previously described or be contained in or co-administered with one or more known drugs.

Among the tests conducted to demonstrate the anxiolytic activity of the present compounds was the Shock-Induced Suppression of Drinking (Rats) (SSD) Test, described in *Pharmacology Biochemistry & Behavior*, Vol. 12, pp. 819–821 (1980) which was carried out as follows:

Male Wistar rats in the weight range of 200 to 220 grams are deprived of water for 48 hours and deprived of food for 24 hours before testing. Normally the rats are orally intubated (5 ml/kg) with the test compound at dosage levels of 6.25, 12.5, 25 and 50 mg/kg body weight. (The test compound is administered intraperitoneally in a few instances). The vehicle control group of rats is also intubated by mouth. A positive control group of rats is also orally administered a control dose of 18 mg/kg of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, N.J. When intraperitoneal (i.p.) administration is used, the protocol is identical except that the drugs are administered (5 ml/kg) 30 minutes prior to testing. Dosages are varied by varying the concentration of drug in the 5 ml volume. The rat is placed on the floor in the chamber facing a licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each 20th lick is paired with a 0.5 mA shock. This period is automatically started, counted and terminated. The number of licks and shocks are recorded. The activity of the compound tested is evaluated by comparing the mean shocks of the group dosed with the test compound to the mean shocks of the vehicle group via a Students' t-test. In general, an increase in the number of shocks received compared to the control is indicative of the anti-conflict or anti-anxiety activity of the compound. The difference is regarded as statistically significant if the probability P that the difference is due to chance in the Students' t-test is less than 0.05.

A second test for anxiolytic activity conducted on compounds of the invention was the [$^3$H]flunitrazepam binding test described in the *European Journal of Pharmacology*, Vol. 78, pp. 315–322 (1982) by B. A. Meiners and A. I. Salama, which was conducted as follows:

A lysed mitochondrial-synaptosomal (P$_2$) fraction was prepared from the cerebral cortex of male Sprague-Dawley rats weighing 150–250 g, according to the method of Braestrup and Squires in the *Proceedings of the National Academy of Science U.S.A.*, Vol. 74, p. 3805 (1977). The fraction was then washed twice by centrifugation in 50 millimolar Tris-Citrate pH 7.4 buffer containing 100 millimolar NaCl.

Specific flunitrazepam binding was measured by a filtration assay similar to that of Wastek et al. in the *European Journal of Pharmacology*, Vol. 50, p. 445 (1978). The 2 ml assays contained 0.2 nM [$^3$H]flunitrazepam (84 Curie/mmol) and membranes equivalent to 10 mg fresh weight (0.2 mg protein) in 50 millimolar Tris-Citrate pH 7.4 buffer containing 100 millimolar NaCl. Drugs were added in 20 μl 95% ethanol which was also added to the control. Non-specific binding was determined in the presence of 2.5 μM clonazepam or 0.5 μM flunitrazepam. The samples were allowed to equilibrate for 90 min. at 0° C. before being filtered and rinsed. Typical assays were done in triplicate. That concentration of test compound causing 50% displacement of [$^3$H]-flunitrazepam relative to a control that contains no added test compound, defined as IC$_{50}$, was determined from at least 5 concentrations (ranging from about 5 to about 500 nanomolar) of test compound using a logit transformation of the data as described by D. B. Bylund in *Receptor Binding Techniques*, published by Society for Neuroscience (1980).

Anxiolytic activity is indicated in the flunitrazepam binding test by a displacement of the flunitrazepam such as is exhibited by benzodiazepines or by enchancement of the binding such as is shown by cartazolate and tracazolate.

A third test called the Forced Motor Activity (FMA) test or rotorod test was run on compounds selected on the basis of the results from the SSD and flunitrazepam tests. This test, conducted to demonstrate the sedative liability of the present compounds is described in the *European Journal of Pharmacology*, Pharmacology, Vol. 78, pp. 323–333 (1982) which is a modification of the method of Kinnard and Carr in *J. Pharmacol. Exp. Therap.*, Vol. 121, page 354 et seq. (1957).

Males Wistar rats, in the weight range of 200–260 grams, are deprived of food for approximately 4–6 hours prior to drug administration. Initially, rats are trained to maintain themselves for at least one-minute on a rotating rod (6 r.p.m.). Then, approximately 2 hours later, groups of at least 8 rats per dose are treated orally with 5 ml/kg volume of either the hydroxypropyl methyl cellulose vehicle (HPMC) or the test compound agent, and tested for their ability to maintain themselves on the rotorod at selected intervals (e.g., 15, 30, and 60 min.) post-drug administration. Dosages are varied by varying the concentration of drug in the 5 ml volume. Random selection of rats is utilized in dosing. Any subject which fails to stay on the rotating rod for the one-minute test duration is considered to be neuromuscularly imparied (ataxic). The ED$_{50}$ (i.e., that dose of test agent that would be predicted to significantly affect 50% of the rats tested) for rotorod impairment is calculated by the method of Litchfield and Wilcoxon in *J. Pharmacol. Exp. Therap.* Vol. 96, page 99 et seq. (1949). The ED$_{50}$ for the most preferred compound was about 180 mg/kg.

All compounds of the formula (I) tested showed activity in the rat SSD test, as indicated by a significant increase in the number of shocks received at dosage levels of 50 mg/kg or less, or exhibited significant binding as described above in the [$^3$H]flunitrazepam binding ($^3$H-FNB) test. The most active compounds, as indicated by these tests, were those indicated above as particularly preferred or preferred, i.e., 4-amino-6,7-dihydro-1-pentyl-6-(2-propenyl)cyclopenta[b]pyrazolo[4,3-e]pyridin-5(1H)-one (particularly preferred); 4-amino-1-pentyl-6-(2-propenyl)-5H-1,6,7,8-tetrahydropyrazolo[3,4-b]quinolin-5-one (preferred); and 4-amino-6,7-dihydro-1-pentyl-6-propylcyclopenta[b]pyrazolo[4,3-e]pyridin-5(1H)-one (preferred).

A compound which showed activity in the rotorod test was 4-amino-6,7-dihydro-1-pentyl-6-(2-propenyl)-cyclopenta[b]pyrazolo[4,3-e]pyridin-5(1H)-one.

None of the compounds of the formula (I) which have been tested in the above-mentioned tests has exhibited any signs of toxicity.

Novel intermediates of the invention include those of the formula (IV).

The following examples describe synthesis of compounds of the invention, with all temperatures being in degrees Centigrade (C) and the following abbreviations being used: mg (milligrams), kg (kilograms), g (grams), mM (millimoles), ml (milliliters), mm (millimeters), M (molar), N (normal), mp (melting point), bp (boiling point), tlc (thin layer chromatography), NMR (nuclear magnetic resonance), MS (mass spectrum), m/e (mass to charge ratio), ca (about), DMF (dimethylformamide), THF (tetrahydrofuran), HPMA (hexamethylphosphoric triamide), and DBU (1,8-diazabicyclo[5.4.0]undec-7-ene). Conventional chemical abbreviations for the elements, e.g., C, H, N, and O, are also used. Ambient or room temperature designates 23°±3°. Unless otherwise specified solvent ratios are on a volume:-volume basis. $^1$H NMR measurements were recorded on either a Varian EM-360 or a Brukker 250 MHz instrument. Chemical shifts (δ) are reported in parts per million (ppm) relative to internal tetramethylsilane. Proton-proton coupling constants are expressed in Hz.

EXAMPLE 1

5-Amino-1-pentyl-4-cyanopyrazole (Formula II, R$^1$=pentyl, R$^2$=H)

A warm solution of 6.02 g (49.3 mM) ethoxymethylenemalononitrile in 20 ml of ethanol was added via a cannula with stirring to a solution of 6.04 g (59.1 mM) of pentylhydrazine in 20 ml ethanol maintained at 50°. The mixture was then heated to reflux for 30 minutes, then cooled in a refrigerator (ca 3°) for 18 hours. The white crystalline precipitate was filtered to afford 7.73 g (88%) of the title compound; mp, 143°–144°; tlc, $R_f$=0.50, silica gel, methanol:chloroform (1:19).

EXAMPLE 2 a.

5-(1-Oxo-2-cyclohexen-3-yl)amino-1-pentyl-4-cyano-pyrazole (Formula IV, $R^1$=pentyl, $R^2=R^4=R^5=R^6=R^8=R^9$=H, n=1)

To a stirred suspension of 0.83 g (7.42 mM) of 1,3-cyclohexanedione in 30 ml of toluene was added 1.18 g (6.63 mM) of the pyrazole prepared in Example 1 and about 70 mg para-toluenesulfonic acid monohydrate. The reaction was heated to reflux with collection of the toluene/water azeotrope in a Dean-Stark trap. After 3 hours at reflux, the reaction was cooled to room temperature and diluted with 20 ml of diethyl ether:THF (1:1). An equal volume of saturated aqueous $Na_2CO_3$ was added and the mixture vigorously shaken in a separatory funnel. After the layers were separated, the organic phase was washed once with brine, dried over anhydrous $MgSO_4$ and concentrated to leave a brown gum. Rapid elution through a small amount of silica gel and removal of the solvent afforded a light yellow solid; 1.67 g (93%); mp, 115°–116.5°; tlc, $R_f$=0.22, silica gel, methanol:chloroform (1:19).

b.

4-Amino-1-pentyl-5H-1,6,7,8-tetrahydropyrazolo[3,4-b]quinolin-5-one (Formula I, $R^1$=pentyl, $R^2=R^3=R^4=R^5=R^6=R^7=R^8=R^9$=H, n=1)

Commercial $ZnCl_2$ (12 g, 88 mM) was dried by heating to 150° under high vacuum for one hour. After the dried material had cooled to room temperature under a stream of dry $N_2$, 20 ml of xylenes containing the dissolved enamine from Example 2a (1.65 g, 6.10 mM) were added. The mixture was quickly heated to vigorous reflux with mechanical stirring of the heterogeneous mixture. After 2 hours at reflux, the reaction mixture was cooled to ambient temperature and the xylenes removed. The resultant residue was partitioned between water and a mixture of THF:$CH_2Cl_2$ (1:1) and the layers separated. The aqueous phase was extracted with THF:$CH_2Cl_2$ (1:1), and the extract was combined with the organic phase. The combined organic phase was washed twice with distilled water, and shaken with 10% aqueous NaOH, then shaken with saturated aqueous citric acid before separation of the aqueous alkaline layer from the organic phase. The two phases were then separated, and the organic phase was washed once with brine, then dried and concentrated to leave a light brown solid. Redissolution in $CH_2Cl_2$, filtration through silica gel eluting with ethyl acetate: hexane (1:3) afforded a light brown solid, which was recrystallized from tert-butyl methyl ether/hexane to give 0.68 g (41%) of a crystalline solid; mp, 153°–154°; tlc, $R_f$=0.41, silica gel, methanol:chloroform (1:19); MS, m/e 272.

Elemental Analysis:

Calculated for $C_{15}H_{20}N_4O$: C, 66.15; H, 7.39; N, 20.56.

Found: C, 65.73; H, 7.39; N, 20.77.

EXAMPLE 3 a.

5-(1-Oxo-2-cyclopenten-3-yl)amino-1-pentyl-4-cyanopyrazole (Formula IV, $R^1$=pentyl, $R^2=R^4=R^5=R^6=R^7$=H, A=a direct link)

A mixture of 0.71 g (3.99 mM) of the pyrazole prepared in Example 1 and 0.45 g (4.60 mM) of 1,3-cyclopentanedione was heated in 40 ml of ethylene dichloride containing a catalytic amount of para-toluenesulfonic acid. The water/ethylene dichloride azeotrope was removed over a 3-hour period via a Dean-Stark trap. After cooling to ambient temperature the mixture was stirred vigorously with 10 ml of saturated aqueous $Na_2CO_3$, then diluted with diethyl ether. The layers were separated and the aqueous phase extracted once with ether. The combined ether layer was washed with brine, dried over anhydrous $MgSO_4$ and concentrated to leave a solid. Recrystallization from tert-butyl methyl ether afforded 0.64 g (62%) of the title compound; mp, 131°–133°, tlc, $R_f$=0.08, silica gel, methanol: chloroform (3:97).

b.

4-Amino-6,7-dihydro-1-pentylcyclopenta[b]pyrazolo[4,3-e]pyridin-5(1H)-one (Formula I, $R^1$=pentyl, $R^2=R^3=R^4=R^5=R^6=R^7$=H, A=a direct link)

The enamine described in Example 3a plus an additional sample made from an identical run (0.76 g, 2.94 mM) were added as a solution in 5 ml methylene chloride to dry $ZnCl_2$ (24 g, 177 mM) with mechanical stirring under a nitrogen atmosphere. The mixture was heated to 180° during which a slow stream of dry $N_2$ purged the reaction vessel, thereby removing volatilized methylene chloride. After being heated at 180° for 2 hours, the mixture was cooled to ambient temperature and water added. The resulting mixture was then partitioned between the water and an organic phase consisting of THF:diethyl ether: methylene chloride (5:2:1). The layers were separated and the organic phase washed once with water followed by shaking with 5% aqueous NaOH. A few ml of saturated aqueous citric acid were added to the separatory funnel and the mixture reshaken to give two clear phases. The layers were separated, and the organic phase was washed with brine, dried over anhydrous $MgSO_4$ and concentrated to leave a crude solid. The crude solid was dissolved in a small amount of solvent, filtered through a short silica gel plug, and recrystallized from tert-butyl methyl ether to afford 0.33 g (43%); mp, 172°–173°; tlc, $R_f$=0.30, silica gel, methanol:chloroform (1:19): MS, m/e 258.

Elemental Analysis:

Calculated for $C_{14}H_{18}N_4O$: C, 65.07; H, 7.02; N, 21.68.

Found: C, 64.46; H, 6.97; N, 21.39.

EXAMPLE 4 a. 3-Ethoxy-6-ethyl-2-cyclohexenone (Formula IX, $R^4=R^{10}$=ethyl, $R^5=R^6=R^7=R^8=R^9$=H, n=1)

To a 0° solution of 1.61 ml (1.16 g, 11.5 mM) of diisopropylamine in 25 ml THF was added dropwise 6.97 ml of a 1.65 M solution (11.5 mM) of n-butyllithium in hexane. After stirring 10 minutes, the solution (now containing 11.5 mM of lithium diisopropylamide) was cooled to −78° in a dry ice/acetone bath and 1.46 ml (140 g, 10.0 mM) of 3-ethoxy-2-cyclohexenone dissolved in a few ml of THF added dropwise. This resulted in formation of the enolate ion of 3-ethoxy-2-cyclohexenone. The resulting mixture was stirred for one hour at −78°, after which 2.40 ml (4.68 g, 30 mM) of iodoethane were added. The cooling bath was removed and the mixture warmed to ambient temperature. At this point 1.0 ml of dry HMPA was added and the reaction mixture stirred 45 minutes. Water (ca 10 ml) was cautiously added, followed by 25 ml of diethyl ether. The layers were separated and the organic phase washed once with water, then once with brine. The organic phase was dried over anhydrous $MgSO_4$ and the volatiles then removed, giving an orange-brown oil which was fractionated by chromatography over silica gel. Elution with ethyl acetate:hexane (1:3) and concentraton of the eluate fractions gave the desired alkylated ketone as 1.60 g (95%) of a light yellow oil; tlc, $R_f$=0.16, silica gel, ethyl acetate:hexane (1:3), $^1H$ NMR($CDCl_3$): 5.28δ (s,1H), 3.88δ (q,2H), 1.35δ (t,3H), 0.90δ (t,3H).

b. 4-Ethyl-1,3-cyclohexanedione (Formula III, $R^4$=ethyl, $R^5$=$R^6$=$R^7$=$R^8$=$R^9$=H, n=1)

To a solution of the ketone prepared in Example 4a (1.6 g, 9.5 mM) in 10 ml of THF was added 30 ml of 10% aqueous HCl at room temperature. The mixture was stirred vigorously at room temperature for 3 hours. The aqueous phase was saturated with NaCl, diethyl ether was added and the layers separated. After a single wash with an equal volume of brine, the organic phase was dried ($MgSO_4$) and then concentrated to leave a very viscous light yellow gum; tlc, $R_f$=0.06, silica gel, methanol:chloroform (1:19).

c. 5-(1-Oxo-6-ethyl-2-cyclohexen-3-yl)amino-1-pentyl-4-cyanopyrazole (Formula IV, $R^1$=pentyl, $R^2$=$R^5$=$R^6$=$R^7$=$R^8$=$R^9$=H, $R^4$=ethyl, n=1)

A mixture of 1.26 g (9.0 mM) of the diketone prepared in Example 4b and 1.78 g (10.0 mM) of the pyrazole described in Example 1 were heated together in 20 ml toluene containing a catalytic amount of para-toluenesulfonic acid. The toluene/water azeotrope was removed in a Dean-Stark trap with about 2 hours required for near theoretical removal of water. The mixture was cooled to ambient temperature and the crude product isolated as described in Example 2a. The product was purified by column chromatography over silica gel using ethyl acetate:hexane (1:2) as the eluent. There was obtained 1.94 g (72%) of the title compound; tlc, $R_f$=0.25, silica gel, ethyl acetate:hexane (1:1).

d. 4-Amino-6-ethyl-1-pentyl-5H-1,6,7,8-tetrahydropyrazolo[3,4b]quinolin-5-one (Formula I, $R^1$=1-pentyl, $R^2$=$R^3$=$R^5$=$R^6$=$R^7$=$R^8$=$R^9$=H, $R^4$=ethyl, n=1)

A solution of 1.94 g (6.46 mM) of enamine prepared as described in Example 4c in a few ml of methylene chloride was added to 52.8 g (388 mM) of solid, mechanically stirred dry $ZnCl_2$ under nitrogen. The mixture was heated to 180° under a stream of dry $N_2$ to remove volatilized methylene chloride, and maintained at 180° for 1 hour. The mixture was cooled to ambient temperature and the crude product isolated as described in Example 3b. The crude product was recrystallized from diethyl ether/hexane to afford 1.15 g (59%) of the title compound as white crystals: mp, 95°–96.5°, MS, m/e 300.

Elemental Analysis:
Calculated for $C_{17}H_{24}N_4O$: C, 67.97; H, 8.05; N, 18.65.
Found: C, 67.69; H, 8.09; N, 18.45.

EXAMPLE 5 a. 3-Ethoxy-6-propyl-2-cyclohexenone (Formula IX, $R^4$=propyl, $R^5$=$R^6$=$R^7$=$R^8$=$R^9$=H, $R^{10}$=ethyl, n=1)

The enolate anion derived from 3-ethoxy-2-cyclohexenone (1.74 ml, 12.0 mM) was prepared as described in Example 4a at −78° using 1.93 ml (13.8 mM) diisopropylamine and 8.36 ml (13.8 mM) of 1.65 n-butyllithium in 25 ml of THF. To this solution was added 2.08 ml (12.0 mM) HMPA in a small amount of THF followed by 2.34 ml (24 mM) of 1-iodopropane. The mixture was warmed to ambient temperature with stirring for 1.5 hours. The title compound was isolated as described in Example 4a as a light yellow oil in an amount of 1.12 g (51%); tlc, $R_f$=0.28, silica gel, ethyl acetate:hexane (1:3).

b. 4-Propyl-1,3-cyclohexanedione (Formula III, $R^4$=propyl, $R^5$=$R^6$=$R^7$=$R^8$=$R^9$=H, n=1)

The title compound was prepared as described in Example 4b except that 1.11 g (6.1 mM) of the ketone prepared in Example 5a and 25 ml of 10% aqueous hydrochloric acid in 10 ml THF were used. Following the work-up there was isolated 1.0 g (quantitative) of the desired propylcyclohexanedione as a thick gum; tlc, $R_f$=0.21, silica gel, methanol:chloroform (1:19).

c. 5-(1-Oxo-6-propyl-2-cyclohexen-3-yl)amino-1-pentyl-4-cyanopyrazole (Formula IV, $R^1$=pentyl, $R^2$=$R^5$=$R^6$=$R^8$=$R^9$=H, $R^4$=propyl, n=1)

A mixture of 0.94 g (6.10 mM) of the diketone prepared in Example 5b and 1.07 g (6.0 mM) of the pyrazole produced in Example 1 were heated together in 40 ml of toluene containing a catalytic amount of para-toluenesulfonic acid. The toluene/water azeotrope was removed in a Dean-Stark trap over a period of 2 hours. The mixture was cooled to ambient temperature and the crude product isolated as described in Example 2a. The title compound was obtained as a yellow oil after isolation by chromatography over silica gel using ethyl acetate:hexane (1:4) as the eluent. There was obtained 1.70 g (90%); tlc, $R_f$=0.10, silica gel, ethyl acetate:hexane (1:3).

d. 4-Amino-1-pentyl-6-propyl-5H-1,6,7,8-tetrahydropyrazolo[3,4b]quinolin-5-one (Formula I, $R^1$=pentyl, $R^2$=$R^3$=$R^5$=$R^6$=$R^7$=$R^8$=$R^9$=H, $R^4$=propyl, n=1)

The title compound was prepared according to the procedure described in Example 3b except 1.70 g (5.41 mM) of the enamine prepared in Example 5c was cyclized using 44 g (325 mM) of dry $ZnCL_2$. The crude product obtained was filtered through a short silica gel plug using ethyl acetate:hexane (1:3) as the eluent. Concentration yielded a solid, which was recrystallized from diethyl ether/hexane to yield 1.34 g (79%) of the desired product; mp, 94°–95°; tlc, $R_f$=0.37, silica gel, ethyl acetate: hexane (1:3); MS, m/e 314.

Elemental Analysis:
Calculated for $C_{18}H_{26}N_4O$: C, 68.76; H, 8.34; N, 17.82.
Found: C, 68.73; H, 8.44; N, 18.01.

EXAMPLE 6 a. 3-Ethoxy-6-methyl-2-cyclohexenone (Formula IX, $R^4$=methyl, $R^5=R^6=R^7=R^8=R^9$=H, $R^{10}$=ethyl, n=1)

A solution of lithium diisopropylamide was prepared as described in Example 4a by combining 8.36 ml of a 1.65 M solution (13.8 mM) of n-butyllithium in hexane and 1.93 ml (13.8 mM) of diisopropylamine in 25 ml THF at 0°, and cooling to −78°. To this was added at −78° 1.74 ml (12 mM) of 3-ethoxy-2-cyclohexenone in a few ml of THF. The mixture was stirred 1 hour at −78°, after which time 1.50 ml (24 mM) of iodomethane was added followed by 2.08 ml (12 mM) of HMPA. The cooling bath was removed and the mixture warmed to ambient temperature with stirring for 2 hours. Water was added and the crude product worked-up as described in Example 4a. The product was purified by column chromatography over silica gel, using ethyl acetate:hexane (1:4) as the eluent. There was obtained 1.56 g (84%) of the title compound; tlc, $R_f$=0.20, silica gel, ethyl acetate:hexane (1:3).

b. 4-Methyl-1,3-cyclohexanedione (Formula III, $R^4$=methyl, $R^5=R^6=R^7=R^8=R^9$=H, n=1)

The ketone prepared in Example 6a (1.56 g, 10.1 mM) was hydrolyzed according to the procedure outlined in Example 4b. There was isolated 1.34 g (quantitative) of a thick gum: tlc, $R_f$=0.23, silica gel, methanol:chloroform (1:19).

c.
5-(1-Oxo-6-methyl-2-cyclohexen-3-yl)amino-1-pentyl-4-cyanopyrazole (Formula IV, $R^1$=pentyl, $R^2=R^5=R^6=R^7=R^8=R^9$=H, $R^4$=methyl, n=1)

The title compound was prepared as described in Example 2a, utilizing 1.34 g (10.1 mM) of the diketone prepared in Example 6b and 1.78 g (10 mM) of the pyrazole produced in Example 1. The title compound was obtained as a brown-orange oil which was chromatographed over silica gel with ethyl acetate:hexane (3:7) as the eluent. The fractions containing the desired compound were combined and concentrated to leave a colorless oil, 2.47 g (86%); tlc, $R_f$=0.06, silica gel, ethyl acetate:hexane (1:3).

d.
4-Amino-6-methyl-1-pentyl-5H-1,6,7,8-tetrahydropyrazolo[3,4-b]quinolin-5-one (Formula I, $R^1$=pentyl, $R^2=R^3=R^5=R^6=R^7=R^8=R^9$=H, $R^4$=methyl, n=1)

The title compound was prepared as described in Example 3b utilizing 2.47 g (8.6 mM) of the enamine obtained in Example 6c and 71 g (518 mM) of dry $ZnCl_2$. Recrystallization of the product from tert-butyl methyl ether/hexane afforded 1.91 g (77%) of a white powder; mp, 128°–129.5°; tlc, $R_f$=0.28, silica gel, ethyl acetate:hexane (1:3): MS, m/e 286.
Elemental Analysis:
Calculated for $C_{16}H_{22}N_4O$: C, 67.10; H, 7.75: N, 19.56.
Found: C, 66.97; H, 7.65; N, 19.71.

EXAMPLE 7

3-(2-Methyl-1-propyloxy)-2-cyclopentenone (Formula IX, $R^4=R^5=R^6=R^7$=H, $R^{10}$=2-methyl-1-propyl, A=a direct link)

To a mixture of 90 ml each of 2-methyl-1-propanol and toluene at room temperature were added 10.0 g (102 mM) of 1,3-cyclopentanedione and 0.3 g (1.5 mM, 1.5%) para-toluenesulfonic acid. The mixture was heated to reflux and the water/toluene/2-methyl-1-propanol azeotrope removed in a Dean-Stark trap. Within 3 hours, the theoretical amount of water (about 1.8 ml) had been removed. Most of the volatiles were removed by distillation at atmospheric pressure and the mixture was then cooled to ambient temperature. The residue was taken up in diethyl ether and washed once with saturated aqueous $NaHCO_3$. A final wash with brine was followed by drying over anhydrous $Na_2SO_4$ and then by removal of the ether. The residue was distilled (bp=66°–69° at 0.05 mm Hg) to afford a colorless liquid which solidified upon cooling in an ice-bath to give 14.5 g (92%); tlc, $R_f$=0.20, silica gel, ethyl acetate:hexane (2:5): $^1$H NMR $(CDCl_3)$=5.27δ (S,1H), 3.73δ (d,2H), 2–2.6δ (m,5H), 0.97δ (d,6H).

EXAMPLE 8 a.
3-(2-Methyl-1-propyloxy)-5-methyl-2-cyclopentenone (Formula IX, $R^4$=methyl, $R^5=R^6=R^7$=H, $R^{10}$=2-methyl-1-propyl, A=a direct link)

A solution of lithium diisopropylamide was prepared by dropwise addition of 9.1 ml (15 mM) of a 1.65 M solution of n-butyllithium in hexane to a solution of 2.10 ml (15 mM) of diisopropylamine in 30 ml THF at 0°. The solution was then cooled to −78° and 2.28 g (14.8 mM) of the ketone prepared in Example 7 in a few ml THF added dropwise. The resulting solution was stirred one hour at −78°. To this solution was added 1.62 ml (26 mM) of iodomethane followed by 1.74 ml (10 mM) HMPA. The solution was stirred for one hour at −78°, then warmed to ambient temperature. After 2 hours at room temperature, water and then diethyl ether were added. The layers were separated and the organic phase washed once with brine, dried over anhydrous $MgSO_4$ and concentrated to leave a brown oil. Purification by column chromatography over silica gel, with ethyl acetate:hexane (3:7) as the eluent, afforded 1.49 g (60%) of a yellow oil; tlc, $R_f$=0.32, silica gel, ethyl acetate:hexane (2:5).

b. 4-Methyl-1,3-cyclopentanedione (Formula III, $R^4$=methyl, $R^5=R^6=R^7$=H, A=a direct link)

The ketone prepared in Example 8a (1.49 g, 8.87 mM) was subjected to the hydrolytic conditions described in Example 4b. However, in this case warming to 40° for several hours was necessary to complete the reaction. Work-up according to the procedure of Example 4b afforded 0.86 g (94%) of a yellow gum: tlc, $R_f$=0.05, ethyl acetate:hexane (2:5).

c.
5-(1-Oxo-5-methyl-2-cyclopenten-3-yl)amino-1-pentyl-4-cyanopyrazole (Formula IV, $R^1$=pentyl, $R^2=R^5=R^6=R^7$=H, $R^4$=methyl, A=a direct link)

The diketone prepared in Example 8b (0.86 g, 7.67 mM) was mixed with 1.35 g (7.60 mM) of the pyrazole described in Example 1 in 25 ml of toluene along with a catalytic amount of para-toluenesulfonic acid. The mixture was heated to reflux with collection of the water/toluene azeotrope in a Dean-Stark trap. After complete removal of water, the mixture was cooled to ambient temperature and the crude product isolated as described in Example 2a. The crude product was purified by column chromatography over silica gel using ethyl acetate:hexane (1:1) as the eluent. The fractions containing the desired product were combined and concentrated to leave a yellow solid 1.47 g (71%); tlc, $R_f=0.08$, silica gel, ethyl acetate:hexane (1:1).

d.
4-Amino-6,7-dihydro-6-methylcyclopenta[b-]pyrazolo[4,3-e]pyridin-5(1H)-one (Formula I, $R^1=$pentyl, $R^2=R^3=R^5=R^6R^7=H$, $R^4=$methyl, A = a direct link)

To solid, mechanically stirred dry $ZnCl_2$ (57 g, 420 mM) under a $N_2$ atmosphere was added the enamine from Example 8c (1.47 g, 5.41 mM). The mixture was then heated to 180° with stirring for 2.5 hours to effect complete reaction. After the mixture was cooled to ambient temperature, water was added and the crude product isolated as described in Example 3b, then purified by filtration through a short silica gel plug and recrystallization from tert-butyl methyl ether/hexane to give the title compound as a white solid, 0.58 g (39%); mp, 156.5°-158°; tlc, $R_f=0.14$, silica gel, ethyl acetate:hexane (1:3); MS, m/e 272.

Elemental Analysis:
Calculated for $C_{15}H_{20}N_4O$: C, 66.15; H, 7.40; N, 20.57.
Found: C, 65.80; H, 7.42: N, 20.50.

EXAMPLE 9 a. 3-(2-Methyl-1-propyloxy)-5-ethyl-2-cyclopentenone (Formula IX, $R^4=$ethyl, $R^5=R^6=R^7=H$, $R^{10}=$2-methyl-1-propyl, A=a direct link)

The title compound was prepared as described in Example 4a except as otherwise indicated. 2.41 g (15.6 mM) of the ketone obtained from Example 7 was employed. The lithium diisopropylamide solution was generated as described also in Example 4a but using 9.58 ml (15.8 mM) of 1.65 M n-butyllithium and 2.21 ml (15.8 mM) diisopropylamine in 30 ml THF. Added to this solution were 2.61 ml (15 mM) of HMPA and 2.28 ml (28.6 mM) of iodoethane. After work-up the crude product was purified by chromatography over silica gel using ethyl acetate:hexane (1:3) as the eluent. The fractions containing the desired compound were combined and concentrated to leave 1.16 g (41%) of a clear oil; tlc, $R_f=0.25$, silica gel, ethyl acetate:hexane (1:3).

b. 4-Ethyl-1,3-cyclopentanedione (Formula III, $R^4=$ethyl, $R^5=R^6=R^7=H$, A=a direct link)

The ketone prepared in Example 9a, 1.16 g (6.36 mM), was subjected to the hydrolysis conditions described in Example 4b using 22 ml of 10% aqueous hydrochloric acid and 15 ml THF. Following the work-up procedure described previously in Example 4b there was obtained 0.68 g (85%) of a yellow oil.

c.
5-(1-Oxo-5-ethyl-2-cyclopenten-3-yl)amino-1-pentyl-4-cyanopyrazole (Formula IV, $R^1=$pentyl, $R^4=$ethyl, $R^2=R^5=R^6=R^7=H$, A=a direct link)

The title compound was prepared as described in Example 2a except that 0.68 g (5.39 mM) of the diketone prepared in Example 9b was reacted with 1.15 g (6.50 mM) of the pyrazole produced in Example 1. The crude product was purified by column chromatography over silica gel using ethyl acetate:hexane (3:7) as the eluent. The fractions containing the title compound were combined and concentrated to leave 0.89 g (58%).

d.
4-Amino-6,7-dihydro-6-ethyl-1-pentylcyclopenta-[b]-pyrazolo[4,3-e]pyridin-5(1H)-one (Formula I, $R^1=$pentyl, $R^2=R^3=R^5=R^6=R^7=H$, $R^4=$ethyl, A=a direct link)

The title compound was prepared according to the procedure described in Example 3b except that 0.89 g of the enamine prepared in Example 9c was reacted with 27 g (200 mM) of dry $ZnCl_2$ and only methylene chloride was used to extract the final product. Recrystallization of the product from tert-butyl methyl ether yielded 0.46 g (52%) of a white crystalline solid; mp, 148°-149°: tlc, $R_f=0.24$, silica gel, ethyl acetate:hexane (1:1); MS, m/e 286.

Elemental Analysis: Calculated for $C_{16}H_{22}N_4O$: C, 67.10; H, 7.75; N, 19.56. Found: C, 67.15: H, 7.71; N, 19.63.

EXAMPLE 10 a. (3E)-3-Hepten-2-one (Formula VII, $R^6=$propyl, $R^7=H$)

To a room temperature suspension of 1.67 g (38 mM) of sodium hydride (55% in oil) which had been washed twice with dry diethyl ether and resuspended in 125 ml of fresh diethyl ether was added dropwise 7.38 g (38 mM) of acetonyl diethyl phosphonate. The resulting suspension was stirred vigorously with a mechanical stirrer until most of the gas evolution had ceased (about 30 minutes). The mixture was cooled to ice-bath temperature and 3.34 ml (38 mM) of freshly distilled butanal contained in a few ml of ether added dropwise. Upon completion of the addition the cooling bath was removed and the mixture warmed to 40° with stirring for 2 hours. After the mixture was cooled to ambient temperature, water was added and the layers separated. The ethyl ether layer was washed sequentially with equal volumes of saturated $NaHCO_3$ and brine. After being dried over anhydrous $MgSO_4$, the ether was carefully removed by distillation at atmospheric pressure. Distillation of the residue under reduced pressure afforded 0.75 g (18%) of a sweet-smelling colorless liquid; bp=56°-59° at 25 mm Hg.* *The procedure in this paragraph follows the directions given in J. K. Crandall et al., *Journal of Organic Chemistry*, Vol. 35, p. 3049–3053 (1970).

b. 4-Carbomethoxy-5-propyl-1,3-cyclohexanedione (Formula III-A, $R^4=R^5=R^7=H$, $R^6$propyl, $R^{12}=$methyl)

Freshly cut sodium metal (0.19 g, 8.3 mM) was reacted with 10 ml of dry methanol at room temperature. After complete reaction 1.05 ml (9.18 mM) of dimethyl malonate was added and the solution stirred 15 minutes. To this solution was added 0.73 g (6.65 mM) of the enone produced in Example 10a. The mixture was then heated to gentle reflux with stirring for 3.5 hours. After cooling of the mixture and removal of most of the methanol using aspirator vacuum, 10 ml of water were added and the aqueous phase extracted twice with chloroform. The pH of the aqueous phase was reduced to 3 to 4 by careful dropwise addition of concentrated hydrochloric acid. Sodium chloride was added to saturate the aqueous phase, which was then extracted twice with 10 ml diethyl ether. The ether layer was dried over MgSO$_4$ and concentrated to dryness to yield 1.99 g (quantitative) of a white amorphous solid: tlc, R$_f$=0.67, silica gel, methanol:chloroform (1:19).

c. 5-Propyl-1,3-cyclohexanedione (Formula III, R$^4$=R$^5$=R$^7$=R$^8$=R$^9$=H, R$^6$=propyl, n=1)

The diketone produced in Example 10b was stirred with 12 ml of aqueous 10% sodium hydroxide at 100° for 2.5 hours. After cooling for ca 15 minutes, 3 ml of concentrated hydrochloric acid were added and the mixture again heated to 100° for an additional 1 hour. After cooling the mixture to ambient temperature, sodium chloride was added to saturate the aqueous phase, which was then extracted twice with diethyl ether. The ether layer was washed once with brine, dried over MgSO$_4$ and concentrated to leave a viscous yellow oil which slowly solidified upon standing to 1.08 g (quantitative): tlc, R$_f$=0.23, silica gel, methanol:chloroform (1:19). Tlc analysis also revealed a very minor component at R$_f$=0.65 in the sample.

d. 5-(1-Oxo-5-propyl-2-cyclohexen-3-yl)amino-1-pentyl-4-cyanopyrazole (Formula IV, R$^1$=pentyl, R$^2$=R$^4$=R$^5$=R$^7$=R$^8$=R$^9$=H, R$^6$=propyl, n=1)

A mixture of 1.08 g (7.01 mM) of the diketone produced in Example 10c and 1.20 g (7.08 mM) of the pyrazole from Example 1 was heated in 25 ml of toluene containing a catalytic amount of para-toluenesulfonic acid. The water/toluene azeotrope was removed in a DeanStark trap and the crude product isolated as described in Example 2a. The crude material was purified by column chromatography over silica gel employing ethyl acetate:hexane (3:7) as the eluent. Combination of the fractions containing the desired product, followed by removal of the volatiles, left the title compound as a thick gum: tlc, R$_f$=0.15, ethyl acetate:hexane (2:5).

e. 4-Amino-1-pentyl-7-propyl-5H-1,6,7,8-tetrahydropyrazolo[3,4-b]quinolin-5-one (Formula I, R$^1$=pentyl, R$^2$=R$^3$=R$^4$=R$^5$=R$^7$=R$^8$=R$^9$=H, R$^6$=propyl, n=1)

The title compound was prepared according to the procedure described in Example 3b except that 0.94 g (2.99 mM) of the enamine prepared in Example 10d was reacted with 27 g (200 mM) of dry ZnCl$_2$ After heating as described previously, the crude product was isolated as described in Example 3b. After filtering through a short silica gel plug eluting with ethyl acetate:hexane (1:3), the title compound was recrystallized from tert-butyl methyl ether/hexane to give 0.64 g (68%) of a white powder; mp, 100.5°102°: tlc, R$_f$=0.21, ethyl acetate:hexane (1:3); MS, m/e 314.

Elemental Analysis: Calculated for C$_{18}$H$_{26}$N$_4$O: C, 68.76; H, 8.34; N, 17.82. Found: C, 68.67; H, 8.27; N, 17.85.

EXAMPLE 11 a. 6-Butyl-3-ethoxy-2-cyclohexenone (Formula IX, R$^4$=butyl, R$^5$=R$^6$=R$^7$=R$^8$=R$^9$=H, R$^{10}$=ethyl, n=1)

A solution of lithium diisopropylamide was prepared as described in Example 4a using 8.36 ml of a 1.65 M solution (13.8 mM) of n-butyllithium in hexane and 1.93 ml (13.8 mM) of diisopropylamine dissolved in 25 m dry THF. The enolate anion of 3-ethoxy-2-cyclohexenone, 1.74 ml (12.0 mM), was then generated from the aforementioned solution of lithium diisopropylamide as described in Example 4a. 1-Iodobutane (2.72 ml, 24 mM) was added as the alkylating agent and 2.08 m (12.0 mM) of HMPA was added as a cosolvent. After aqueous work-up there was obtained a crude oil which was purified by column chromatography over silica gel using ethyl acetate:hexane (1:3) as the eluent to afford 1.19 g (51%) of the title compound; tlc, R$_f$=0.33, silica gel, ethyl acetate: hexane (1:3).

b. 4-Butyl-1,3-cyclohexanedione (Formula III, R$^4$=butyl, R$^5$=R$^6$=R$^7$=R$^8$=R$^9$=H, n=1)

A solution of 1.19 g (6.06 mM) of the ketone prepared in Example 11a was subjected to the hydrolysis conditions outlined in Example 4b using 25 ml of 10% aqueous hydrochloric acid and 10 ml of THF as a solvent. After work-up there was obtained 0.91 g (89%) of a clear, colorless oil; tlc, R$_f$=0.31, methanol:chloroform (1:19).

c. 5-(1-Oxo-6-butyl-2-cyclohexen-3-yl)amino-1-pentyl-4-cyanopyrazole (Formula IV, R$^1$=pentyl, R$^2$=R$^5$=R$^6$=R$^7$=R$^8$=R$^9$=H, R$^4$=butyl, n=1)

The title compound was prepared as described in Example 2a except that 0.91 g (5.41 mM) of the diketone produced in Example 11b was reacted with 0.95 g (5.35 mM) of the pyrazole prepared in Example 1. The crude product was purified by column chromatography over silica gel using ethyl acetate:hexane (3:7) as the eluent. The fractions containing the desired product were combined and the solvent removed to afford 1.28 g (73%) of a clear, viscous oil; tlc, R$_f$=0.25, ethyl acetate:hexane (1:1).

d. 4-Amino-6-butyl-1-pentyl-5H-1,6,7,8-tetrahydropyrazolo[3,4-b]quinolin-5-one (Formula I, R$^1$=pentyl, R$^2$=R$^3$=R$^5$=R$^6$=R$^7$=R$^8$=R$^9$=H, R$^4$=butyl, n=1).

The title compound was prepared according to the procedure outlined in Example 3b except that 1.28 g (3.90 mM) of the enamine described in Example 11c was used, and 53 g (234 mM) of anhydrous ZnBr$_2$ was substituted for ZnCl$_2$. Following work-up, the crude product was passed through a short silica gel plug with ethyl acetate:hexane (1:3) as eluent, then recrystallized from tert-butyl methyl ether/hexane. There was obtained 1.06 g (83%) of a white solid; mp, 58.5°–60°; tlc, R$_f$=0.24, ethyl acetate: hexane (1:3): MS, m/e 328.

Elemental Analysis: Calculated for C$_{19}$H$_{28}$N$_4$O: C, 69.45; H, 8.59; N, 17.06. Found: C, 69.47: H, 8.60; N, 17.13.

EXAMPLE 12 a. 3-Ethoxy-6-(2-propenyl)-2-cyclohexenone (Formula IX, R$^4$=2propenyl, R$^5$=R$^6$=R$^7$=R$^8$=R$^9$=H, R$^{10}$=ethyl, N=1)

A solution of lithium diisopropylamide was prepared as described in Example 4a using 8.36 ml of a 1.65 M solution (13.8 mM) of n-butyllithium in hexane and 1.93 ml (13.8 mM) of diisopropylamine in 25 ml of dry THF. The enolate derived from 1.74 ml (12.0 mM) of 3- ethoxy-2-cyclohexenone was prepared as also described in Example 4a, but reacted with 2.08 ml (24 mM) of 3-bromopropene instead of iodoethane as the alkylating agent in the presence of 2.08 ml (12.0 mM) of HMPA. Following work-up analogous to that previously detailed in Example 4a, there was obtained a crude brown oil. Purification by column chromatography over silica gel using ethyl acetate:hexane (1:4) as the eluent afforded 1.97 g (91%) of the title compound as a yellow oil; tlc, $R_f=0.29$, silica gel, ethyl acetate:hexane (1:3).

b. 4-(2-Propenyl)-1,3-cyclohexanedione (Formula III, $R^4$=2-propenyl, $R^5=R^6=R^7=R^8=R^9$=H, n=1)

The ketone prepared in Example 12a (1.97 g, 10.9 mM) was hydrolyzed to the diketone by a procedure analogous to that described in Example 4b, except that 30 ml of 10% aqueous hydrochloric acid and 15 ml THF were used. Following work-up as in Example 4b there was obtained 1.52 g (92%) of a clear gum; tlc, $R_f=0.28$, silica gel, methanol:chloroform (1:19).

c.
5-(1-Oxo-6-(2-propenyl)-2-cyclohexen-3-yl)amino-1-pentyl-4-cyanopyrazole (Formula IV, $R^1$=pentyl, $R^2=R^5=R^6=R^7=R^8=R^9$=H, $R^4$=2-propenyl, n=1)

A procedure analogous to that employed in Example 2a was followed except 1.52 g (10 mM) of the diketone prepared in Example 12b was reacted with 1.75 g of the pyrazole described in Example 1. The crude product was purified by chromatography over silica gel, eluting with ethyl acetate:hexane (3:7) to give 2.52 g (82%) of the title compound as a thick yellow oil; tlc, $R_f=0.25$, silica, ethyl acetate:hexane (1:1).

d.
4-Amino-1-pentyl-6-(2-propenyl)-5H-1,6,7,8-tetrahydropyrazolo[3,4-b]quinolin-5-one (Formula I, $R^1$=pentyl, $R^2=R^3=R^5=R^6=R^7=R^8=R^9$=H, $R^4$=2-propenyl, n=1)

The enamine (2.52 g, 8.07 mM) described in Example 12c was used to prepare the title compound following the procedure described in Example 3b except that 66 g (484 mM) of dry $ZnCl_2$ was used to effect cyclization. The crude product was passed through a small silica gel plug, eluted with ethyl acetate:hexane (3:7), and recrystallized from tert-butyl methyl ether/hexane to yield 1.70 g (67%) of a crystalline solid: mp, 95°–96.5°; tlc, $R_f=0.20$, silica gel, ethyl acetate:hexane (1:3): MS, m/e 312.

Elemental Analysis: Calculated for $C_{18}H_{24}N_4O$: C, 69.20: H, 7.74; N, 17.93. Found: C, 69.05: H, 7.84; N, 18.15.

EXAMPLE 13 a. (3E)-3-Octen-2-one (Formula VII, $R^6$=butyl, $R^7$=H)

A solution of 7.73 g (58 mM) of anhydrous LiI and 1.47 ml (20 mM) of acetone in 35 ml of diethyl ether was heated to gentle reflux. To this solution was added dropwise a solution of 1.59 ml (15.0 mM) 1-pentanal in 5 ml diethyl ether over 10 minutes. The solution was then heated at reflux for 6 hours. After the solution was cooled to ambient temperature water was added and the layers separated. The ether phase was washed once with brine and dried over anhydrous $MgSO_4$. The diethyl ether was removed by distillation at atmospheric pressure followed by distillation of the residue. There was obtained 0.52 g (27%) of a highly mobile colorless liquid. $^1H$ NMR ($CDCl_3$):6.80δ (dt,1H,$J_{HH}$=7Hz, 16Hz), 6.01δ (d,1H,$J_{HH}$=16Hz), 2.20δ (s,3H).

b. 4-Carbomethoxy-5-butyl-1,3-cyclohexanedione (Formula III-A, $R^6$=butyl, $R^5=R^7=R^8=R^9$=H, $R^{12}$=methyl)

A procedure like that employed in Example 10b was followed using the ketone obtained from Example 13a plus an additional quantity of the same material (0.88 g, 6.97 mM), but with the following changes in the amounts of reagents: sodium, 0.20 g (8.71 mM): dimethyl malonate, 1.09 ml (9.58 mM); and methanol, 8 ml. The crude product was isolated in an identical manner to that described in Example 10b as a colorless oil which solidified upon standing to 1.71 g (quantitative).

c. 5-Butyl-1,3-cyclohexanedione (Formula III, $R^6$=butyl, $R^4=R^5=R^7=R^8=R^9$=H, n=1)

The diketone produced in Example 13b was stirred with 13 ml of aqueous 10% sodium hydroxide at 100° for 2.5 hours. After cooling to ambient temperature the reaction mixture was washed once with diethyl ether. The ether layer was discarded and the aqueous phase acidified with 3.5 ml of concentrated hydrochloric acid then heated to 100° for an additional 1 hour. After cooling to ambient temperature, the aqueous phase was carefully basified with solid potassium carbonate and washed once with ether. The ether layer was discarded and the aqueous phase re-acidified with concentrated hydrochloric acid to a pH of less than 3. Sodium chloride was added to saturate the aqueous phase and the aqueous layer extracted twice with equal volumes of ether. The ether extracts were combined and washed once with brine, dried over anhydrous $MgSO_4$ and concentrated to leave 1.11 g (95%) of a light yellow gum which solidified upon standing; tlc, $R_f=0.26$, silica gel, methanol:chloroform (1:19).

d.
5-(1-Oxo-5-butyl-2-cyclohexen-3-yl)amino-1-pentyl-4-cyanopyrazole (Formula IV, $R^1$=pentyl, $R^2=R^4=R^5=R^7=R^8=R^9$=H, $R^6$=butyl, n=1)

A procedure like that described for Example 2a was followed except that 1.11 g (6.6 mM) of the diketone prepared in Example 13c was reacted with 1.14 g (6.4 mM) of the pyrazole described in Example 1. The crude product was purified by column chromatography over silica gel using ethyl acetate:hexane (2:5) as the eluent. There was obtained 1.77 g (84%) of a very viscous yellow oil.

e.
4-Amino-7-butyl-1-pentyl-5H-1,6,7,8-tetrahydropyrazolo[3,4-b]quinolin-5-one (Formula I, $R^1$=pentyl, $R^2=R^3=R^4=R^5=R^7=R^8=R^9$=H, $R^6$=butyl, n=1)

To a suspension of 67 g (300 mM) of anhydrous zinc bromide was added a solution of the enamine produced in Example 13d (1.41 g, 4.3 mM) in a few ml of methylene chloride. The mechanically stirred mixture was heated slowly to 180° during which a constant stream of dry nitrogen gas purged the reaction vessel to remove volatilized methylene chloride. After heating ca 1 hour at 180°, the reaction mixture was cooled to ambient temperature and the product isolated in an identical fashion to that described in Example 2b. The crude product was purified by first passing it through a short silica gel plug with ethyl acetate:hexane (1:1) as to the eluent. Recrystallization from tert-butyl methyl ether/hexane then afforded the title compound as 0.77 g (55%) of a white crystalline solid; mp, 92°–93°; tlc, $R_f$=0.36, silica gel, ethyl acetate: hexane (1:1): MS, m/e 328.

Elemental Analysis: Calculated for $C_{19}H_{20}N_4O$: C, 69.45; H, 8.59; N, 17.06. Found: C, 69.33; H, 8.23; N, 17.02.

EXAMPLE 14 a.
3-(2-Methyl-1-propyloxy)-5-propyl-2-cyclopentenone (Formula IX, $R^4$=propyl, $R^5$=$R^6$=$R^7$=H, $R^{10}$=2-methyl-1-propyl, A=a direct link)

A solution of lithium diisopropylamide was generated as described in Example 4a using 12.3 ml of a 1.65 M solution (20.3 mM) of n-butyllithium in hexane and 2.86 ml (20.4 mM) of diisopropylamine in 35 ml dry THF. The ketone prepared in Example 7 was used to form the corresponding enolate at −78° as also described in Example 4a. HPMA (3.13 ml, 18 mM) was added as the cosolvent, followed by 1-iodopropane (3.91 ml, 40 mM) as the alkylating agent. The crude product was purified by column chromatography over silica gel using ethyl acetate:hexane (1:3) as the eluent. There was obtained 0.89 g (23%) of the title compound; tlc, $R_f$=0.34, silica gel, ethyl acetate:hexane (1:1).

b. 4-Propyl-1,3-cyclopentanedione (Formula III, $R^4$=propyl, $R^5$=$R^6$=$R^7$=H, A=a direct link)

The ketone prepared in Example 14a was combined with a sample from a duplicate run and the combined sample (1.79 g, 8.52 mM) hydrolyzed according to the procedure outlined in Example 4b. There was obtained 1.03 g (86%) of a thick, slightly yellow oil; tlc, $R_f$=0.15, silica gel, methanol:chloroform (1:19).

c.
5-(1-Oxo-5-propyl-2-cyclopenten-3-yl)amino-1-pentyl-4-cyanopyrazole (Formula IV, $R^1$=pentyl, $R^2$=$R^5$=$R^6$=$R^7$=H, $R^4$=propyl, A=a direct link)

The title compound was prepared by heating together 1.05 g (7.5 mM) of the diketone prepared in Example 14b with 1.28 g (7.2 mM) of the pyrazole produced in Example 1 in 25 ml toluene according to the procedure of Example 2a. The crude product obtained from work-up was purified by column chromatography over silica gel using ethyl acetate:hexane (2:5) as the eluent. The fractions containing the desired product were combined and concentrated to leave 1.01 g (47%) of a white solid; tlc, $R_f$=0.13, silica gel, ethyl acetate:hexane (1:1).

d.
4-Amino-6,7-dihydro-1-pentyl-6-propylcyclopenta[b-]pyrazolo[4,3-e]pyridin-5(1H)-one (Formula I, $R^1$=pentyl, $R^2$=$R^3$=$R^5$=$R^6$=$R^7$=H, $R^4$=propyl, A=a direct link)

To 46 g (202 mM) of dry zinc bromide at room temperature was added the solid enamine produced in Example 14c (1.01 g, 3.37 mM). The mechanically stirred mixture was then slowly heated under nitrogen to 180° with stirring for 2 hours. After cooling to ambient temperature, water was added and the mixture partitioned between THF/methylene chloride and water. The layers were separated and the aqueous phase extracted once with THF/methylene chloride. The combined organic phase was washed twice with water, then shaken with an equal volume of 10% aqueous sodium hydroxide. Enough saturated aqueous citric acid was added to the mixture, with intermittent shaking, to completely dissolve the inorganic precipitates. The organic phase was washed once with brine, dried over $MgSO_4$ and concentrated to leave a yellow-brown oil. Filtration of the oil through a short silica gel plug and elution with ethyl acetate:hexane (1:1) left a white solid. Recrystallization from tert-butyl methyl ether afforded 0.67 g (66%) of white crystals: mp, 138°–139°; tlc, $R_f$=0.21, silica gel, ethyl acetate:hexane (1:1): MS, m/e 300.

Elemental Analysis: Calculated for $C_{17}H_{24}N_4O$: C, 67.97; H, 8.05; N, 18.65. Found: C, 67.95; H, 8.24; N, 18.29.

EXAMPLE 15 a.
3-(2-Methyl-1-propyloxy)-5-(2-propenyl)-2-cyclopentenone (Formula IX, $R^4$=2-propenyl, $R^{10}$=2-methyl-1-propyl, $R^5$=$R^6$=$R^7$=H, A=a direct link)

A solution of lithium diisopropylamide was generated as described in Example 4a using 16.7 ml of a 1.65 M solution (27.5 mM) of n-butyllithium in hexane and 3.85 ml (27.5 mM) of diisopropylamine dissolved in 40 ml THF. The ketone prepared in Example 7 was used to form the corresponding enolate anion at −78° as also described in Example 4a. To this was added dropwise a solution of allyl iodide in THF which was prepared in the following way. To a suspension of dry sodium iodide (12.0 g, 80 mM) in 30 ml THF were added 5.18 ml (6.0 mM) of 3-bromopropene. The flask was covered with aluminum foil to exclude the light and the contents stirred vigorously overnight (ca 14 hours). The solids were allowed to settle and the supernatant was decanted via a cannula under nitrogen pressure into another flask containing a small amount of $CaH_2$. The dark colored solution of the iodide was stirred 10 minutes over the calcium hydride and the sediment allowed to settle. The supernatant containing excess allyl iodide was then used to react with the aforementioned enolate anion. After stirring the reaction had been stirred 2 hours at −78°, the cooling bath was removed and the mixture warmed slowly to room temperature. After 1 hour at ambient temperature, water was added, followed by some diethyl ether to dilute the organic phase. The layers were separated and the organic phase washed once with brine, then dried over $MgSO_4$ and concentrated to a brown oil. Column chromatography over silica gel, using ethyl acetate:hexane (3:7) as the eluent, gave 2.81 g (54%) of the title compound; tlc, $R_f$=0.51, silica gel, ethyl acetate:hexane (1:1). There was also recovered 1.06 g of the starting ketone.

b. 4-(2-Propenyl)-1,3-cyclopentanedione (Formula III, $R^4$=2propenyl, $R^5$=$R^6$=$R^7$=H, A=a direct link)

The ketone prepared in Example 15a (2.81 g, 74.4 mM) was hydrolyzed as described in Example 4b to give 1.86 g (93%) of a clear, very thick gum; tlc, $R_f$=0.13, silica gel, methanol: chloroform (1:19).

c.
5-(1-Oxo-5-(2-propenyl)-2-cyclopenten-3-yl)amino-1-pentyl-4cyanopyrazole (Formula IV, $R^1$=pentyl, $R^2=R^5=R^6=R^7$=H, $R^4$=2-propenyl, A=a direct link)

The title compound was prepared by heating together 1.86 g (13.5 mM) of the diketone produced in Example 15b with 2.31 g (13.0 mM) of the pyrazole described in Example 1 in 30 ml of toluene as described in Example 2a. The crude product obtained was purified by column chromatography over silica gel using ethyl acetate:hexane (1:1) as the eluent. The resulting solid from concentration of the fractions containing the desired proudct was recrystallized from tert-butylmethyl ether with a little hexane to afford 2.01 g (78%) of the title compound, tlc, $R_f$=0.14, silica gel, ethyl acetate:hexane (1:1).

d.
4-Amino-6,7-dihydro-1-pentyl-6-(2-propenyl)cyclopenta[b]pyrazolo[4,3-e]pyridin-5(1H)-one (Formula I, $R^1$=pentyl, $R^2=R^3=R^5=R^6=R^7$=H, $R^4$=2-propenyl, A=a direct link)

To a room temperature solution of 1.47 g (4.90 mM) of the enamine described in Example 15c in 10 ml n-butyl acetate under a nitrogen atmosphere was added 1.20 g (9.78 mM) of copper (I) acetate. The mixture was stirred 10 minutes at ambient temperature, then plunged into an oil bath preheated to 130°. The mixture was stirred vigorously for 10 minutes, then removed from the oil bath and cooled to room temperature. To the mixture was added 5 ml of concentrated ammonium hydroxide followed by 5 ml water. The mixture was stirred 15 minutes, then diluted with diethyl ether. The very dark blue aqueous phase was separated and extracted twice with ethyl ether:THF (1:1). The combined organic phase was washed once with brine, dried over $MgSO_4$, concentrated and filtered through a small plug of silica gel. Recrystallization of the solid from tert-butylmethyl ether/hexane gave 1.28 g (87%) of fine white crystals; mp, 141.5°-142.5°; tlc, $R_f$=0.31, silica gel, ethyl acetate:hexane (1:1), MS, m/e 298.

Elemental Analysis: Calculated for: C, 68.43: H, 7.43; N, 18.78. Found: C, 68.58; H, 7.71; N, 18.65.

EXAMPLE 16 a.
3-(2-methyl-1-propyloxy)-5,5-dimethyl-2-cyclopentenone (Formula IX, $R^4=R^5$=methyl, $R^6=R^7$=H, $R^{10}$=2-methyl-1-propyl, A=a direct link)

A solution of lithium diisopropylamide was generated as described in Example 4a using 11.5 ml of a 1.65 M solution (19.0 mM) of n-butyllithium in hexane and 2.66 ml (19.0 mM) of diisopropylamine in 35 ml THF. The ketone (3.27 g, 18.0 mM) prepared in Example 8a was used to form the corresponding enolate, which was then reacted with 2.24 ml (36.0 mM) of iodomethane in the presence of 3.2 ml (18 mM) of HMPA as described in Example 4a. The crude product was purified by column chromatography over silica gel using ethyl acetate:hexane (1:4) as the eluent. The fractions containing the title compound were combined and concentrated to leave 3.09 g (94%) of a slightly yellow oil; tlc, $R_f$=0.33, silica gel, ethyl acetate:hexane (1:3). $^1$H NMR ($CDCl_3$) 5 13δ (S,1H), 3.72δ (d,2H), 2.43δ (S,2H), 2.0-2.1 (m,1H), 1.13δ (S,6H), 0.98δ (d,6H).

b. 4,4-Dimethyl-1,3-cyclopentanedione (Formula III, $R^4=R^5$=methyl, $R^6=R^7$=H, A=a direct link)

The ketone produced in Example 16a (3.09 g, 16.9 mM) was hydrolyzed and isolated according to the procedure outlined in Example 4b. There were obtained 2.0 g (94%) of a light yellow gum; tlc, $R_f$=0.16, silica gel, methanol:chloroform (1:19).

c.
5-(1-Oxo-5,5-dimethyl-2-cyclopenten-3-yl)amino-1-pentyl-4cyanopyrazole (Formula IV, $R^1$=pentyl, $R^2=R^6=R^7$=H, $R^4=R^5$=methyl, A=a direct link)

A mixture of 1.44 g (11.4 mM) of the diketone prepared in Example 16b and 1.78 g (10 mM) of the pyrazole described in Example 1 were heated in 30 ml of toluene according to the procedure described in Example 2a. Following work up according to Example 2a the crude product was purified by column chromatography over silica gel using ethyl acetate:hexane (1:1) as the eluent to yield 2.24 g (78%) of the title compound; tlc, $R_f$=0.09, silica gel, ethyl acetate:hexane (1:1).

d.
4-Amino-6,7-dihydro-6,6-dimethyl-1-pentylcyclopenta[b]pyrazolo[4,3-e]pyridin-5(1H)-one (Formula I, $R^1$=pentyl, $R^2=R^3=R^6=R^7$=H, $R^4=R^5$=methyl, A=a direct link)

The enamine (2.20 g, 7.68 mM) produced in Example 16c was cyclized according to the procedure outlined in Example 3b except that 64 g (470 mM) of dry $ZnCl_2$ were used. The crude product was filtered through a small plug of silica gel with ethyl acetate:hexane (1:1) as the eluent. The material thus obtained was recrystallized from methylene chloride/hexane to give 1.65 g (75%) of the title compound as white crystals: mp, 170°; tlc, $R_f$=0.11, silica gel, ethyl acetate:hexane (1:3); MS, m/e 286.

Elemental Analysis: Calculated for $C_{16}H_{22}N_4O$: C, 67.10; H, 7.74; N, 19.56. Found: C, 67.18: H, 7.80: N, 19.51.

EXAMPLE 17 a. 3-Ethoxy-6-(1-methylethyl)-2-cyclohexenone (Formula IX, $R^4$=1methylethyl, $R^5=R^6=R^7=R^8=R^9$=H, $R^{10}$=ethyl, n=1)

A solution of lithium diisopropylamide was prepared according to the procedure of Example 4a using 9.82 ml of a 1.65 M solution (16.2 mM) of n-butyllithium in hexane and 2.27 ml (16.2 mM) of diisopropylamine in 30 ml THF. The enolate anion derived from 2.18 ml (15.0 mM) of 3-ethoxy-2-cyclohexenone was generated as also described in Example 4a. In this example (17a) HMPA (3.0 ml) was added as a cosolvent, followed by 2.99 ml (30 mM) of 2-iodopropane. Subsequently there was obtained a crude yellow oil which was purified by column chromatography over silica gel employing ethyl acetate:hexane (1:4) as the eluent. The fractions containing the desired product were combined and concentrated to leave 0.52 g (19%) of the title compound: tlc, $R_f$=0.36, silica gel, ethyl acetate:hexane (1:3).

b. 4-(1-Methylethyl)-1,3-cyclohexanedione (Formula III, $R^4=$ 1-methylethyl, $R^5=R^6=R^7=R^8=R^9=H$, n=1)

The ketone prepared in Example 17a was subjected to the hydrolysis conditions outlined in Example 4b to give 0.45 g (quantitative) of a white solid; tlc, $R_f=0.27$, silica gel, methanol:chloroform (1:19).

c. 5-(1-Oxo-6-(1-methylethyl)-2-cyclohexen-3-yl)amino-1-pentyl4-cyanopyrazole (Formula IV, $R^1=$pentyl, $R^2=R^5=R^6=R^7=R^8=R^9=H$, $R^4=$ 1-methylethyl, n=1)

The diketone (0.48 g, 2.85 mM) prepared in Example 17b was reacted with 0.50 g (2.80 mM) of the pyrazole prepared in Example 1 according to the procedure outlined in Example 2a. Following the work-up procedure, the crude product was purified by column chromatography on silica gel employing ethyl acetate:hexane (2:5) as the eluent. The fractions containing the desired product were combined and concentrated to yield 0.80 g (91%) of a white solid: tlc, $R_f=0.23$, silica gel, ethyl acetate:hexane (1:1).

d. 4-Amino-1-pentyl-6-(1-methylethyl)-5H-1,6,7,8-tetrahydropyrazolo[3,4-b]quinolin-5-one (Formula I, $R^1=$pentyl, $R^4=$ 1-methylethyl, $R^2=R^3=R^5=R^6=R^7=R^8=R^9=H$, n=1)

The enamine (0.80 g, 2.55 mM) prepared in Example 17c was cyclized according to the procedure described in Example 3b except that 20 g (150 mM) of dry $ZnCl_2$ were used. The resulting crude product was filtered through a short plug of silica gel, then recrystallized from tert-butyl methyl ether/hexane. There was obtained 0.78 g (99%) of the title compound as a white crystalline solid; mp, 114.5°–116.5°; tlc, $R_f=0.44$, silica gel, ethyl acetate:hexane (1:1); MS, m/e 314.

Elemental Analysis:
Calculated for $C_{18}H_{26}N_4O$: C, 68.76; H, 8.34; N, 17.82.
Found: C, 68.63; H, 8.17; N, 17.71.

EXAMPLE 18 a. 3-Ethoxy-6-benzyl-2-cyclohexenone (Formula IX, $R^4=$benzyl, $R^5=R^6=R^7=R^8=R^9=H$, $R^{10}=$ethyl, n=1)

A solution of lithium diisopropylamide was prepared according to the procedure of Example 4a using 8.36 ml of a 1.65 M solution (13.8 mM) of n-butyllithium in hexane and 1.93 ml (13.8 mM) of diisopropylamine in 25 ml THF. 3-Ethoxy-2-cyclohexenone 1.75 ml (12.0 mM) in a few ml dry THF was added dropwise to the solution of lithium diisopropylamide at −78°. Following a stirring interval of 1 hour at −78° C., HMPA (2.08 ml, 12 mM) (dissolved in a few ml dry THF) was added, followed by 2.76 ml (24 mM) benzyl chloride instead of iodoethane. The reaction was stirred 15 minutes at −78°, then warmed to ambient temperature with stirring for 2 hours. Several ml of water were then added and the mixture extracted with ethyl ether. The organic phase was washed once with an equal volume of brine, dried over anhydrous magnesium sulfate and concentrated to leave a brown oil. Purification of the crude product by column chromatography over silica gel using ethyl acetate:hexane (1:4) as the eluent afforded 1.06 (38%) of the title compound; tlc, $R_f=0.22$, ethyl acetate:hexane (1:3).

b. 4-Benzyl-1,3-cyclohexanedione (Formula III, $R^4=$benzyl, $R^5=R^6=R^7=R^8=R^9=H$, n=1)

The ketone prepared in Example 18a (1.06 g, 4.6 mM) was hydrolyzed according to the conditions described in Example 4b to yield 0.82 g (88%) of a white solid; tlc $R_f=0.27$, silica gel, methanol:chloroform (1:19).

c. 5-(1-Oxo-6-benzyl-2-cyclohexen-3-yl)amino-1-pentyl-4-cyanopyrazole (Formula IV, $R^1$pentyl, $R^2=R^5=R^6=R^7=R^8=R^9=H$, $R^4=$benzyl, n=1)

The diketone (0.82 g, 4.05 mM) described in Example 18b was reacted with 0.70 g (3.95 mM) of the pyrazole prepared in Example 1 by the procedure of Example 2a. The resulting crude product was purified by column chromatography over silica gel using ethyl acetate:hexane (2:5) as the eluent. Combination of the fractions containing the desired compound and subsequent concentration left 0.82 g (57%) of a thick gum; tlc, $R_f=0.23$, silica gel, ethyl acetate:hexane (1:1).

d. 4-Amino-6-benzyl-1-pentyl-5H-1,6,7,8-tetrahydropyrazolo[3,4-b]quinolin-5-one (Formula I, $R^1=$pentyl, $R^2=R^3=R^5=R^6=R^7=R^8=R^9=H$, $R^4=$benzyl, n=1).

The enamine (0.74 g, 2.04 mM) prepared in Example 18c was cyclized according to the procedure of Example 3b except that 20 g (150 mM) of dry $ZnCl_2$ were used. The resulting crude product was filtered through a short silica gel plug, then recrystallized from tert-butyl methyl ether to afford 0.43 g (58%) of the title compound as a white solid; mp, 105°–108°; tlc, $R_f=0.24$, silica gel, ethyl acetate:hexane (1:3); MS, m/e 362.

Elemental Analysis:
Calculated for $C_{22}H_{26}N_4O$: C, 72.89; H, 7.23; N, 15.46.
Found: C, 72.96; H, 7.26; N, 15.22.

EXAMPLE 19 a. 3-(2-Methyl-1-propyloxy)-5-(3-buten-1-yl)-2-cyclopentenone (Formula IX, $R^4=$3-buten-1-yl, $R^5=R^6=R^7=H$, $R^{10}=$2-methyl-1-propyl, A = a direct link)

To a suspension of 10.0 g (66 mM) of sodium iodide in 20 ml of dry THF were added 4.51 ml (44 mM) of 4-bromo-1-butene. The mixture was then heated at reflux with stirring overnight (ca 16 hours), then cooled to ambient temperature. The supernatant was decanted from the precipitated salts via a cannula and the residue washed with 10 ml of fresh THF. The resulting supernatant was decanted and combined with the first supernatant to give a solution of crude 4-iodo-1-butene. A solution of lithium diisopropylamide was then generated as described in Example 4a at −78° using 10.0 ml of a 1.65 M solution (16.5 mM) of n-butyllithium in hexane and 2.31 ml (16.5 mM) of diisopropylamine in 35 ml THF. The ketone prepared in Example 7 (2.52 g, 16.3 mM), 2.0 ml of HMPA, and the solution of crude 4-iodo-1-butene prepared as described above, were added to the lithium diisopropylamide solution at −78° according to the procedure of Example 4a. The cooling bath was removed and the mixture warmed to ambient temperature with stirring for 3 hours. Water was then added followed by diethyl ether. The layers were separated and the organic phase washed once with an equal volume of brine, then dried over anhydrous $Na_2SO_4$ and concentrated to a crude product, which was purified by column chromatography over silica gel using ethyl acetate:hexane (2:5) as the eluent. Combination and concentration of the fractions containing the desired product left 1.29 g (36%) of a yellow liquid; tlc, $R_f=0.52$, silica gel, ethyl acetate:hexane (1:1).

b. 4-(3-Buten-1-yl)-1,3-cyclopentanedione (Formula III, $R^4=$3-buten-1-yl, $R^5=R^6=R^7=H$, A=a direct link)

The ketone prepared in Example 19a (1.29 g, 5.81 mM) was hydrolyzed as described in Example 4b. The resulting gum obtained after work-up amounted to 0.84 g (95%).

c. 5-(1-Oxo-5-(3-buten-1-yl)-2-cyclopenten-3-yl)amino-1-pentyl-4-cyanopyrazole (Formula IV, $R^1=$pentyl, $R^2=R^5=R^6=R^7=H$, $R^4=$3-buten-1-yl, A=a direct link)

A mixture of 0.84 g (5.53 mM) of the diketone prepared in Example 19b and 0.88 g (4.94 mM) of the cyanoaminopyrazole described in Example 1 were heated together in 20 ml toluene according to the procedure described in Example 2a. Following work up as in Example 2a, the crude product was purified by column chromatography over silica gel using ethyl acetate:hexane (1:1) as the eluent. The fractions containing the desired product were combined and concentrated to leave 0.92 g (60%) of the title compound: tlc, $R_f=0.17$, silica gel, ethyl acetate:hexane (1:1).

d. 4-Amino-6-(3-buten-1-yl)-6,7-dihydro-1-pentylcyclopenta[b]-pyrazolo[4,3-e]pyridin-5(1H)-one (Formula I, $R^1=$pentyl, $R^2=R^3=R^5=R^6=R^7=H$, $R^4=$3-buten-1-yl, A=a direct link)

The enamine (0.91, 2.91 mM) prepared in Example 19c was cyclized according to the procedure described in Example 15d using 0.72 g (5.83 mM) copper (I) acetate in 5 ml of n-butyl acetate. The mixture was heated under a nitrogen atmosphere at 110° for approximately 25 minutes. After the mixture was cooled to ambient temperature, several ml of concentrated ammonium hydroxide were added, followed by a few ml of water. The mixture was stirred vigorously for 10 minutes after which diethyl ether was added and the layers separated. The aqueous phase was extracted twice with THF:diethyl ether (1:3). The organic phases were combined and washed once with an equal volume of brine, then dried over anhydrous $MgSO_4$ and concentrated to a residue, which was filtered through a silica gel plug. Recrystallization of the crude product from tert-butyl methyl ether/hexane gave 0.65 g (71%) of a white crystalline solid; mp, 138°–139°; tlc, $R_f=0.31$, silica.gel, ethyl acetate: hexane (1:1); MS, m/e 312.

Elemental Analysis:
Calculated for $C_{18}H_{24}N_4O$: C, 69.20; H, 7.74; N, 17.94.
Found: C, 69.13; H, 7.84; N, 17.84.

EXAMPLE 20 a. 3-(2-Methyl-1-propyloxy)-4,5-dimethyl-2-cyclopentenone (Formula IX, $R^4=R^6=$methyl, $R^5=R^7=H$, $R^{10}=$3-methyl-1-propyl, A=a direct link)

A solution of lithium diisopropylamide was prepared by the dropwise addition of 15.5 ml of a 1.65 M solution (25.5 mM) of n-butyllithium in hexane to a solution of 3.57 ml (25.5 mM) diisopropylamine in 25 ml THF at 0°. Following the complete addition of n-butyllithium, the solution was cooled to −78° and a solution of 1.95 g (12.5 mM) of 3-(2-methyl-1-propyloxy)-2-cyclopentenone (Example 7) in a few ml THF was added dropwise. After being stirred for 30 minutes at −78° the solution was warmed to near 0° in an ice-bath with stirring for an additional 30 minutes. To this were added 2.11 ml (34 mM) of iodomethane, and the mixture was stirred at ice-bath temperature for 1 hour. Water was added cautiously followed by diethyl ether. The layers were separated and the organic phase was washed once with an equal volume of brine, dried over anhydrous $MgSO_4$ and concentrated to leave a brown oil. Column chromatography over silica gel using ethyl acetate:hexane (3:7) as the eluent, yielded 0.98 g (43%) of the desired product as a light yellow oil; tlc, $R_f=0.45$, silica gel, ethyl acetate:hexane (1:1).

b. 4,5-Dimethyl-1,3-cyclopentanedione (Formula III, $R^4=R^6=$methyl, $R^5=R^7=H$, A=a direct link)

To a solution of 0.98 g (5 mM) of the ketone described in Example 20a in 10 ml THF at room temperature were added 25 ml of 10% aqueous hydrochloric acid. The mixture was stirred vigorously overnight, then enough 20% aqueous sodium hydroxide was added to bring the pH to above 11. The mixture was diluted with diethyl ether and the layers separated. The aqueous phase was washed once with ethyl ether, then cooled in an ice-bath and acidified to a pH of 1–2 with concentrated hydrochloric acid. The aqueous phase was saturated with sodium chloride and extracted twice with diethyl ether. The combined ether layer was washed once with brine, then dried over anhydrous $MgSO_4$ and concentrated to 0.62 g (98%) of a colorless oil.

c. 5-(1-Oxo-4,5-dimethyl-2-cyclopenten-3-yl)amino-1-pentyl-4-cyanopyrazole (Formula IV, $R^1=$pentyl, $R^2=R^5=R^732$ H, $R^4=R^6=$methyl, A=a direct link)

A mixture of 0.62 g (4.90 mM) of the diketone prepared in Example 20b and 0.84 g (4.66 mM) of the pyrazole prepared in Example 1 were heated together in 20 ml toluene containing a catalytic amount of para-toluenesulfonic acid as described in Example 2a. The crude product obtained after a work-up (also analogous to that in Example 2a) was purified by column chromatography over silica gel using ethyl acetate:hexane (1:3) as the eluent. The fractions containing the product were combined and concentrated to leave 0.69 g (52%) of the title compound; tlc, $R_f=0.15$, silica gel, ethyl acetate:-hexane (1:3).

d.

4-Amino-6,7-dihydro-6,7-dimethyl-1-pentylcyclopenta[b]-pyrazolo[4,3-e]pyridin-5(1H)-one (Formula I, $R^1$=1-pentyl, $R^2$=$R^3$=$R^5$=$R^7$=H, $R^4$=$R^6$=methyl, A=a direct link)

The enamine (0.69 g, 2.41 mM) prepared in Example 20c was cyclized according to the procedure described in Example 15d using 0.54 g (4.82 mM) of copper (I) acetate in 5 ml of n-butyl acetate. The mixture was heated at 125° for 20 minutes then cooled to ambient temperature. Several ml of concentrated ammonium hydroxide and several ml water were added. The mixture was stirred 15 minutes and diluted with diethyl ether. The layers were separated. The aqueous phase was extracted twice with THF/ethyl ether and the combined organic phases were washed once with brine. The organic phase was then dried over anhydrous $Na_2SO_4$ and concentrated to a brown oil. The oil was separated into 2 products by chromatography over silica gel with ethyl acetate:hexane (2:5) as the eluent. The major and more mobile product on tlc corresponded to the trans-dimethylated title compound in a yield of 0.54 g (78%); tlc, $R_f$=0.35, silica gel, ethyl acetate:hexane (1:1); mp, 150°-151°; MS, m/e 286. $^1$H NMR ($CDCl_3$):vicinal coupling between $H^6$ and $H^7$, $J^3H^6H^7$=4.1 Hz.

Elemental Analysis:

Calculated for: C, 67.10; H, 7.76; N, 19.56.

Found: C, 67.14; H, 7.61; N, 19.74.

The minor and less mobile product corresponded to the cisdimethylated title compound; tlc, $R_f$=0.29, silica gel, ethyl acetate:hexane (1:1); mp, 170°-170.5°. $^1$H NMR ($CDCl_3$):vicinal coupling between $H^6$ and $H^7$, $J^3H^6H^7$=7.5 Hz.

EXAMPLE 21 a. 6-(2-Methylpropyl)-3-ethoxy-2-cyclohexenone (Formula IX, $R^4$=2-methylpropyl, $R^5$=$R^6$=$R^7$=$R^8$=$R^9$=H, $R^{10}$=ethyl, n=1)

A solution of lithium diisopropylamide was prepared as described in Example 4a using 10.45 ml of a 1.65 m solution (17.25 mM) of n-butyllithium in hexane and 2.42 ml (17.25 mM) of diisopropylamine dissolved in 40 ml dry THF. The enolate anion of 3-ethoxy-2-cyclohexenone (2.18 ml, 15.0 mM) was then generated from the aforementioned solution of lithium diisopropylamide as described in Example 4a. 1-Iodo-2-methylpropane (8.28 g, 45.0 mM) was added as the alkylating agent followed by 2.61 ml (15.0 mM) of HMPA as a cosolvent. After aqueous work-up as described in Example 4a there was obtained a crude oil which was purified by column chromatography over silica gel using ethyl acetate:hexane (1:2) as the eluent to afford 0.76 g (26%) of the title compound; tlc, $R_f$=0.46, silica gel, ethyl acetate:hexane (1:3).

b. 4-(2-Methylpropyl)-1,3-cyclohexanedione (Formula III, $R^4$=2-methylpropyl, $R^5$=$R^6$=$R^7$=$R^8$=$R^9$=H, n=1)

A solution of 0.76 g (3.87 mM) of the ketone prepared in Example 21a was subjected to the hydrolysis conditions outlined in Example 4b using 15 ml of 10% aqueous hydrochloric acid and 5 ml of THF as solvent. After work-up there was obtained 0.65 g (100%) of a clear oil; tlc, $R_f$=0.10, methanol:chloroform (1:19).

c.

5-(1-Oxo-6-(2-methylpropyl)-2-cyclohexen-3-yl)amino-1-pentyl-4-cyanopyrazole (Formula IV, $R^1$=pentyl, $R^2$=$R^5$=$R^6$=$R^7$=$R^8$=$R^9$=H, $R^4$=2-methylpropyl, n=1)

The title compound was prepared as described in Example 2a except that 0.65 g (3.87 mM) of the diketone produced in Example 21b was reacted with 0.69 g (3.87 mM) of the pyrazole prepared in Example 1. Following work-up as described in Example 2a, the crude product was purified by column chromatography over silica gel using ethyl acetate:hexane (3:7) as the eluent. There was obtained 1.05 g (83%) of an off-white solid: tlc $R_f$=0.33, ethyl acetate:hexane (1:1).

d.

4-Amino-6-(2-methylpropyl)-1-pentyl-5H-1,6,7,8-tetrahydropyrazolo[3,4-b]quinolin-5-one (Formula I, $R^1$=pentyl, $R^2$=$R^3$=$R^5$=$R^6$=$R^7$=$R^8$=$R^9$=H, $R^4$=2-methylpropyl, n=1)

The title compound was prepared according to the procedure outlined in Example 3b except that 1.05 g (3.20 mM) of the enamine described in Example 21c was used and 26.1 g (192 mM) of dry $ZnCl_2$ were used to catalyze the cyclization. Following work-up, the crude product was passed through a short silica gel plug using ethyl acetate:hexane (1:3) as the eluent. Recrystallization from tert-butyl methyl ether/hexane afforded 0.53 g (51%) of white crystals; mp, 86°-87°; tlc, $R_f$=0.42, methanol:chloroform (1:19); MS, m/e 328.

Elemental Analysis:

Calculated for $C_{19}H_{28}N_4O$:C, 69.48; H, 8.59; N, 17.06.

Found: C, 69.24; H, 8.42; N, 17.04.

EXAMPLE 22 a. 6-(3-Butenyl)-3-ethoxy-2-cyclohexenone (Formula IX, $R^4$=3-butenyl, $R^5$=$R^6$=$R^7$=$R^8$=$R^9$=H, $R^{10}$=ethyl, n=1)

A solution of lithium diisopropylamide was prepared as described in Example 4a using 10.45 ml of a 1.65 m solution (17.25 mM) of n-butyllithium in hexane and 2.42 ml (17.25 mM) of diisopropylamine in 40 ml of dry THF. The enolate derived from 2.18 ml (15.0 mM) of 3-ethoxy-2-cyclohexenone was prepared as also described in Example 4a, but reacted with 3.05 ml (30 mM) of 4-bromo-1-butene (instead of iodoethane) in the presence of 2.61 ml (15.0 mM) HMPA. Following work-up analogous to that previously detailed in Example 4a, there was obtained a crude oil. Purification by column chromatography over silica gel using ethyl acetate:hexane (1:3) as the eluent afforded 0.67 g (23%) of the title compound; tlc, $R_f$=0.29, silica gel, ethyl acetate:hexane (1:3).

b. 4-(3-Butenyl)-1,3-cyclohexanedione (Formula III, $R^4$=3-butenyl $R^5$=$R^6$=$R^7$=$R^8$=$R^9$=H, n=1)

The ketone prepared in Example 22a (0.67 g, 3.45 mM) was hydrolyzed to the diketone by a procedure identical to that described in Example 4b, except that 15 ml of 10% aqueous hydrochloric acid and 5 ml THF were used. There was obtained 0.57 g (ca 100%) of a yellow oil; tlc, $R_f$=0.24, silica gel, methanol:chloroform (1:19).

c.

5-(1-Oxo-6-(3-butenyl)-2-cyclohexen-3-yl)amino-1-pentyl-4-cyanopyrazole (Formula IV, $R^1$=pentyl, $R^2=R^3=R^5=R^6=R^7=R^8=R^9$=H, $R^4$=3-butenyl, n=1)

A procedure analogous to that employed in Example 2a was followed except 0.57 g (3.45 mM) of the diketone prepared in Example 22b was reacted with 0.61 g (3.45 mM) of the pyrazole described in Example 1. The crude product was purified by chromatography over silica gel, eluting with ethyl acetate:hexane (1:2) to give 0.95 g (84%) of the title compound as a yellow oil; tlc, $R_f$=0.31, silica gel, ethyl acetate:hexane (1:1).

d.

4-Amino-6-(3-butenyl)-1-pentyl-5H-1,6,7,8-tetrahydropyrazolo[3,4-b]quinolin-5-one (Formula I, $R^1$=pentyl, $R^2=R^3=R^5=R^6=R^7=R^8=R^9$=H, $R^4$=3-butenyl, n=1)

The enamine (0.95 g, 2.91 mM) described in Example 22c was cyclized as described in Example 3b except that 23.8 g (175 mM) of dry $ZnCl_2$ were used. The crude product was passed through a small silica gel plug eluting with ethyl acetate/hexane and recrystallized from tert-butyl methyl ether/hexane to afford a white sticky solid. The solid was dissolved in excess ether through which anhydrous HCl was bubbled. The resulting white solid was removed by filtration, washed with ether and dried to yield 0.30 g; mp, 229°-241°; tlc, $R_f$=0.23 (free base), silica gel, methanol:chloroform, (1:19); MS, m/e 326 (—HCl).

Elemental Analysis:

Calculated for $C_{19}H_{26}N_4O \cdot HCl$: C, 62.88; H, 7.50; N, 15.44.

Found: C, 62.77; H, 7.43; N, 15.39.

EXAMPLE 23

4-Butylamino-6,7-dihydro-1-pentyl-6-(2-propenyl)cyclopenta[b]-pyrazolo[4,3-e]pyridin-5(lH)-one (Formula I, $R^1$=pentyl, $R^2=R^5=R^6=R^7$=H, $R^3$=butyl, $R^4$=2-propenyl, A=a direct link)

A suspension of 4.43 mM of NaH (0.194 g of 55% NaH in an oil dispersion) in dry THF was stirred vigorously for 10 minutes followed by removal of the THF. The NaH was resuspended in 10 ml dry DMF and a solution of 1.20 g (4.02 mM) of the ketone prepared in Example 15d in 2 ml THF added dropwise. After stirring 30 minutes at ambient temperature, 0.68 ml (6.03 mM) of 1-iodobutane was added. After stirring two hours, the mixture was cooled in an ice-bath and quenched cautiously with water. The mixture was extracted twice with ether with the ether layer washed once with brine. After drying over anhydrous $MgSO_4$, the ether layer was concentrated and the resulting crude product purified by chromatographing over silica gel using ethyl acetate: hexane (1:3) as the eluent. After recrystallization from ether/hexane, there was obtained 1.05 g (74%) of a white solid; mp, 72°-73°; tlc, $R_f$=0.59, silica gel, ethyl acetate:hexane (1:1), MS, m/e 354.

Elemental Analysis:

Calculated for $C_{21}H_{30}N_4O$: C, 71.15; H, 8.53; N, 15.81.

Found: C, 71.45; H, 8.53; N, 15.87.

EXAMPLE 24 a. 4-Carboethoxy-4-phenyl-1,3-cyclohexanedione (Formula III-A, $R^4=R^5=R^6=R^7$=H, $R^8$=phenyl, $R^{12}$=ethyl)

Freshly cut sodium metal (0.88 g, 38.1 mM) was reacted with 50 ml of absolute ethanol at room temperature. After complete reaction, 9.40 ml (39 mM) of diethyl phenylmalonate were added. The solution was stirred 20 minutes followed by warming to 40° and adding dropwise 2.7 ml (33.4 mM) of methylvinyl ketone dissolved in 10 ml ethanol. The mixture was heated to reflux with stirring for four hours. The ethanol was removed by distillation followed by cooling and partitioning the mixture between ether and water. The separated aqueous layer was acidified to a pH of 2 and saturated with solid NaCl. Ether was added and the layers separated. The ether layer was washed with brine, dried over anhydrous $MgSO_4$ and concentrated to leave a thick orange gum of 5.02 g (58%).

b. 4-Phenyl-1,3-cyclohexanedione (Formula III, $R^5=R^6=R^7=R^8=R^9$=H, $R^4$=phenyl, n=1).

A similar procedure to that described in Example 10c was followed except 5.02 g (19.3 mM) of the diketoester produced in Example 24a (instead of the diketone) was used along with 35 ml of 10% aqueous sodium hydroxide. After work-up there was obtained 2.18 g (60%) of a brown gum.

c.

5-(1-Oxo-6-phenyl-2-cyclohexen-3-yl)amino-1-pentyl-4-cyanopyrazole (Formula IV, $R^1$=pentyl, $R^2=R^5=R^6=R^7=R^8=R^9$=H, $R^4$=phenyl, n=1)

A procedure and subsequent work-up analogous to that employed in Example 2a were followed except 2.18 g (11.6 mM) of the diketone prepared in Example 24b was reacted with 1.78 g (10.0 mM) of the pyrazole described in Example 1. The crude product was chromatographed over silica gel using ethyl acetate:hexane (1:1) as the eluent. After recrystallization from tert-butyl methyl ether there was obtained 0.74 g (21%) of a white solid; tlc, $R_f$=0.17, silica gel, ethyl acetate:hexane (1:1).

d.

4-Amino-1-pentyl-6-phenyl-5H-1,6,7,8-tetrahydropyrazolo[3,4-b]quinolin-5-one (Formula I, $R^1$=pentyl, $R^2=R^3=R^5=R^6=R^7=R^8=R^9$=H, $R^4$=phenyl, n=1)

The enamine (0.74 g, 2.12 mM) prepared in Example 24c was cyclized according to the procedure described in Example 15d using 0.52 g (4.25 mM) of copper (I) acetate in 3 ml each of butyl acetate and DMF. After work-up the crude product was run through a silica gel plug using ethyl acetate:hexane (1:1) as the eluent. Recrystallization from tert-butyl methyl ether afforded 0.57 g (77%) of a light yellow crystalline solid; mp, 110°-116°; tlc, $R_f$=0.30, silica gel, ethyl acetate:hexane (1:1): MS, m/e 348.

Elemental Analysis:

Calculated for $C_{21}H_{24}N_4O$: C, 72.38; H, 6.94; N, 16.08.

Found: C, 72.43; H, 6.95; N, 16.26.

EXAMPLE 25

4-Amino-6,7-dihydro-1-pentyl-7-(2-propenyl)cyclopenta[b]pyrazolo[4,3-e]pyridin-5(1H)-one (Formula I, $R^1$=pentyl, $R^2$=$R^3$=$R^4$=$R^5$=$R^7$=H, $R^6$=2-propenyl, A=a direct link)

A large scale-up of the reaction described in Example 15c afforded as a by-product the isomeric enamine 5-(1-oxo-4-(2-propenyl)-2-cyclopenten-3-yl)amino-1-pentyl-4-cyanopyrazole (Formula IV, $R^1$=pentyl, $R^2$=$R^4$=$R^5$=$R^7$=H, $R^6$=2-propenyl, A=a direct link). Cyclization of 0.86 g (2.88 mM) of this compound according to the procedure of Example 15d was conducted using 0.70 g (5.76 mM) of copper (I) acetate in butyl acetate:DMF (5 ml:1 ml). After work-up the crude product was passed through a silica gel plug using ethyl acetate:hexane (1:1) as the eluent. Recrystallization from tert-butyl methyl ether gave 0.35 g (41%) of a white solid; mp, 107.5°-109.5°: tlc, $R_f$=0.21, silica gel, ethyl acetate:hexane (1:1): MS, m/e 298.

Elemental Acetate:

Calculated for $C_{17}H_{22}N_4O$: C, 68.43; H, 7.43; N, 18.78.

Found: C, 67.60; H, 7.34; N, 18.62.

EXAMPLE 26 a.

5-Amino-4-cyano-1-(5-trimethylsilyl-4-pentynyl)-pyrazole (Formula II, $R^1$=5-trimethylsilyl-4-pentynyl, $R^2$=H)

A suspension of 5-amino-4-cyanopyrazole (10 g) and finely ground anhydrous potassium carbonate (38 g) in dry DMF (100 ml) was treated with 5-iodo-1-trimethylsilyl-1-pentyne (25 g) and the mixture was stirred under nitrogen for two days at room temperature. The reaction mixture was then poured into water and the product extracted into ethyl acetate. The extract was washed with water and then with brine, dried over $Na_2SO_4$, and evaporated to give a semisolid brown residue. This solid was taken up in chloroform and filtered through a short plug of silica gel. Evaporation of the chloroform left a tan solid comprising a mixture of the isomeric compounds 5-amino-4-cyano-1-(5-trimethylsilyl-4-pentynyl)pyrazole and 3-amino-4-cyano-1-(5-trimethylsilyl-4-pentynyl)pyrazole. Fractional recrystallization from ethyl acetate/hexane gave 4.66 grams of the desired 5-amino-4-cyano-1-(5-trimethylsilyl-4-pentynyl)pyrazole: mp 125°-127°.

b.

5-(1-Oxo-5-(2-propenyl)-2-cyclopenten-3-yl)amino-1-(5-trimethylsilyl-4-pentynyl)-4-cyanopyrazole (Formula IV, $R^1$=5-trimethylsilyl-4-pentynyl, $R^2$=$R^5$=$R^6$=$R^7$=H, $R^4$=2-propenyl, A=a direct link)

The title compound was prepared by heating together 1.0 g (3.99 mM) of the pyrazole from Example 26a with 0.63 g (4.60 mM) of the diketone produced in Example 15b according to the procedure described in Example 2a. The crude product obtained after work-up as in Example 2a was purified over silica gel chromatography using ethyl acetate: hexane (3:7) as the eluent. There was obtained 1.16 g (78%) of an orange gum; tlc, $R_f$=0.16, silica gel, ethyl acetate:hexane (1:1).

c.

4-Amino-6,7-dihydro-1-(4-pentynyl)-6-(2-propenyl)cyclopenta[b]pyrazolo[4,3-e]pyridin-5(1H)-one (Formula I, $R^1$=4-pentynyl, $R^2$=$R^3$=$R^5$=$R^6$=$R^7$=H, $R^4$=2-propenyl, A=a direct link)

A procedure analogous to that described in Example 15d was followed except 1.06 g (2.86 mM) of the enamine described in Example 26b was cyclized with 0.70 g (5.72 mM) of copper (I) acetate in butyl acetate (8 ml) and DMF (2 ml). After work-up, the resulting product was chromatographed over silica gel using ethyl acetate:hexane (3:7) as the eluent. After recrystallization from tert-butyl methyl ether/hexane, there was obtained 0.15 g (14%) of the title compound; mp, 133°-134°; tlc, $R_f$=0.30, silica gel, ethyl acetate:hexane (1:1); MS, m/e 294.

Elemental Analysis:

Calculated for $C_{17}H_{18}N_4O$: C, 69.37; H, 6.16: N, 19.04.

Found: C, 69.06; H, 6.28; N, 18.95.

EXAMPLE 27 a.

5-(1-Oxo-2-cyclohepten-3-yl)amino-1-pentyl-4-cyanopyrazole (Formula IV, $R^1$=pentyl, $R^2$=$R^4$=$R^5$=$R^6$=$R^7$=$R^8$=$R^9$=H, n32 2)

A procedure analogous to that described for Example 2a was followed except 1.41 g (7.93 mM) of the pyrazole described in Example 1 was reacted with 1.00 g (7.93 mM) of 1,3-cycloheptanedione.** The crude product was purified by column chromatography over silica gel using ethyl acetate:hexane (1:3) as the eluent. There was obtained 1.20 g (53%) of a white solid after recrystallization from tert-butyl methyl ether/hexane; tlc, $R_f$=0.16, silica gel, ethyl acetate:hexane (1:3).

**This compound was prepared by method described in R. Noyori, et. al., *J. Amer. Chem. Soc.* Vol. 102, pp. 2095-2096 (1980).

b.

4-Amino-6,7-dihydro-1-pentylcyclohepta[b]pyrazolo[4,3-e]pyridin-5(1H)-one (Formula I, $R^1$=pentyl, $R^2$=$R^3$=$R^4$=$R^5$=$R^6$=$R^7$=$R^8$=$R^9$=H, n=2)

The enamine (1.10 g, 3.84 mM) produced in Example 27a was cyclized according tot he procedure outlined in Example 15d using 0.94 g (7.68 mM) of copper (I) acetate in butyl acetate (7 ml) and DMF (1 ml). After work-up the crude product was passed through a short silica gel plug eluting with ethyl acetate:hexane (1:1). After recrystallization from tert-butyl methyl ether/hexane there was obtained 0.66 g (60%) of white crystals; mp, 124°-125°; tlc, $R_f$=0.27, silica gel, ethyl acetate:hexane (1:1); MS, m/e 286.

Elemental Analysis:

Calculated for $C_{16}H_{22}N_4O$: C, 67.11; H, 7.74; N, 19.56.

Found: C, 67.13; H, 7.72; N, 19.67.

EXAMPLE 28 a. 3-(2-Methyl-1-propyloxy)-2-cycloheptenone (Formula IX, $R^4$=$R^5$=$R^6$=$R^7$=$R^8$=$R^9$=H, $R^{10}$=2-methyl-1-propyl, n=2)

A procedure analogous to that followed for Example 7 was employed except 2.50 g (19.8 mM) of 1,3-cycloheptanedione were reacted with 20 ml each of 2-methyl-1-propanol and toluene. Following completion of the reaction and work-up 2.37 g (66%) of the crude product were obtained as a light yellow oil; tlc, $R_f=0.48$, silica gel, ethyl acetate:hexane (1:1).

b.
3-(2-Methyl-1-propyloxy)-7-(2-propenyl)-2-cycloheptenone (Formula IX, $R^4$=2-propenyl, $R^5=R^6=R^7=R^8=R^9=H$, $R^{10}$=2-methyl-1-propyl, n2)

A solution of lithium diisopropylamide was prepared as described in Example 4a using 9.59 ml of a 1.56 M solution (14.95 mM) of n-butyllithium in hexane and 2.15 ml (15.34 mM) of diisopropylamine in 25 ml dry THF. The enolate anion of the ketone produced in Example 28a (2.37 g, 13.0 mM) was then generated from the aforementioned solution of lithium diisopropylamide as described in Example 4a. 3-Iodopropene (1.42 ml, 15.6 mM) was added and the reaction conducted as described previously in Example 4a, but without the addition of HMPA. There was obtained a crude yellow oil which was chromatographed over silica gel eluting with ethyl acetate:hexane (1:6) to afford 2.33 g (81%) of a clear oil; tlc, $R_f=0.17$, silica gel, ethyl acetate:hexane (1:19).

c. 4-(2-Propenyl)-1,3-cycloheptanedione (Formula III, $R^4$=2-propenyl, $R^5=R^6=R^7=R^8=R^9=H$, n=2)

A solution of 2.30 g (10.34 mM) of the ketone prepared in Example 28b was hydrolyzed according to the procedure summarized in Example 4b using 10 ml each of 10% aqueous hydrochloric acid and THF. After work-up there was obtained 1.55 g (90%) of a light yellow oil; tlc, $R_f=<0.05$, ethyl acetate: hexane (1:3).

d.
4-Amino-6,7-dihydro-1-pentyl-6-(2-propenyl)cyclohepta[b]pyrazolo[4,3-e]pyridin-5(1H)-one (Formula I, $R^1$=pentyl, $R^2=R^3=R^5=R^6=R^7=R^8=R^9=H$, $R^4$=2-propenyl, n=2)

A solution comprising 1.55 g (9.32 mM) of the ketone produced in Example 28c, 1.66 g (9.32 mM) of the pyrazole described in Example 1 and a catalytic amount of para-toluenesulfonic acid in 15 ml toluene were heated under reflux with removal of the toluene/water azeotrope in a Dean-Stark trap. After heating 5 hours, the excess toluene was distilled off and the mixture cooled to ambient temperature. The residue was taken up in ethyl acetate, washed with saturated aqueous Na$_2$CO$_3$, dried over anhydrous MgSO$_4$ and concentrated to an orange oil. Purification by column chromatography over silica gel afforded the title compound as a clear oil: tlc, $R_f=0.50$, ethyl acetate: hexane (1:1). Dissolution in ether followed by bubbling dry HCl through the solution afforded (after recrystallization from ethanol) the hydrochloride salt as a white solid; mp, 224°-228°; MS, m/e 326 (—HCl).

Elemental Analysis: Calculated for C$_{19}$H$_{26}$N$_4$O.HCl: C, 62.88; H, 7.50; N, 15.44. Found: C, 62.85: H, 7.46; N, 15.50.

EXAMPLE 29 a.
6-(3,3-Dichloro-2-propenyl)-3-ethoxy-2-cyclohexenone (Formula IX, $R^4$=3,3-dichloro-2-propenyl, $R^5=R^6=R^7=R^8=R^9=H$, $R^{10}$=ethyl, n=1)

A solution of lithium diisopropylamide was prepared as described in Example 4a using 3.43 ml of a 1.56 M solution (5.35 mM) of n-butyllithium in hexane and 0.75 ml (5.35 mM) of diisopropylamine in 10 ml dry THF. The enolate anion of 3-ethoxy-2-cyclohexenone (0.52 ml, 3.57 mM) was then generated from the aforementioned solution of lithium diisopropylamide as described in Example 4a. 3-Bromo-1,1-dichloropropene*** (0.81 g, 4.28 mM) was added as the alkylating agent. After work-up there was obtained a dark oil which was chromatographed over silica gel using ethyl acetate:hexane (1:4) as the eluent. The title compound was obtained as 0.74 g (83%) of a yellow liquid; tlc, $R_f=0.36$, silica gel, ethyl acetate:hexane (1:3).

***This compound was prepared by the method described in, L. F. Hatch and S. D. Zimmerman, *J. Amer. Chem. Soc.*, Vol. 79, pp. 3091-3093 (1957).

b. 4-(3,3-Dichloro-2-propenyl)-1,3-cyclohexanedione (Formula III, $R^4$=3,3-dichloro-2-propenyl, $R^5=R^6=R^7=R^8=R^9=H$, n=1)

A solution of 0.74 g (2.97 mM) of the ketone prepared in Example 29a was hydrolyzed as described in Example 4b except 3 ml of 20% aqueous sulfuric acid and 5 ml of THF were used. After work-up there was obtained about 0.66 g of a white solid: tlc, $R_f=0.07$, silica gel, ethyl acetate:hexane (1:3).

c.
5-(1-Oxo-6-(3,3-dichloro-2-propenyl)-2-cyclohexen-3-yl)-amino-1-pentyl-4-cyanopyrazole (Formula IV, $R^1$=pentyl, $R^2=R^5=R^6=R^7=R^8=R^9=H$, $R^4$=3,3-dichloro-2-propenyl, n=1)

A procedure analogous to that described in Example 2a was followed except 0.66 g (2.99 mM) of the diketone prepared in Example 29b was reacted with 0.53 g (2.99 mM) of the pyrazole described in Example 1. After work-up, the crude product was purified by column chromatography over silica gel using ethyl acetate:hexane (1:3) as the eluent. There was obtained 1.05 g (92%) of the title compound as a light yellow solid: tlc, $R_f=0.32$, silica gel, ethyl acetate:hexane (1:1).

d.
4-Amino-6-(3,3-dichloro-2-propenyl)-1-pentyl-5H-1,6,7,8-tetrahydropyrazolo[3,4-b]quinolin-5-one (Formula I, $R^1$=pentyl, $R^2=R^3=R^5=R^6=R^7=R^8=R^9=H$, $R^4$=3,3-dichloro-2-propenyl, n=1)

The enamine (1.05 g, 2.75 mM) prepared in Example 29c was cyclized according to the procedure described in Example 15d using 0.67 g (5.51 mM) of copper (I) acetate in 6 ml of n-butyl acetate and 2 ml DMF. Upon completion of the reaction, the crude product isolated as described in Example 15d was passed through a short silica gel plug using ethyl acetate:hexane (2:5) as the eluent. The product was obtained as white crystals following recrystallization from tert-butyl methyl ether/hexane to yield 0.88 g (84%): mp, 130°-131.5°; tlc, $R_f=0.45$, silica gel, ethyl acetate:hexane (1:1): MS, m/e 381.

Elemental Analysis: Calculated for C$_{18}$H$_{22}$N$_4$OCl$_2$: C, 56.70; H, 5.82: N, 14.69. Found: C, 56.19; H, 5.83: N, 14.45.

EXAMPLE 30 a.
5-(3,3-Dichloro-2-propenyl)-3-(2-methyl-1-propyloxy)-2-cyclopentenone (Formula IX, $R^4=$3,3-dichloro-2-propenyl, $R^5=R^6=R^7=H$, $R^{10}=$2-=2-methyl-1-propyl, A=a direct link)

A solution of lithium diisopropylamide was generated as described in Example 4a using 9.56 ml of a 1.56 M solution (14.9 mM) of n-butyllithium in hexane and 2.13 ml (14.9 mM) of diisopropylamine dissolved in 40 ml of dry THF. The enolate anion was then prepared from 2.00 g (12.97 mM) of the ketone produced in Example 7 and the aforementioned solution of lithium diisopropylamide as described in Example 4a. 3-Bromo-1,1-dichloropropene (2.95 g, 15.6 mM) was then added as the alkylating agent. After work-up an oil was obtained. Chromatography of the oil over silica gel with ethyl acetate: hexane (1:3) as the eluent afforded 3.41 g (quantitative) of product; tlc, $R_f=0.29$, silica gel, ethyl acetate:hexane (1:3).

b. 4-(3,3-Dichloro-2-propenyl)-1,3-cyclopentanedione (Formula III, $R^4=$3,3-dichloro-2-propenyl, $R^5=R^6=R^7=H$, A=a direct link)

The ketone prepared in Example 30a (3.41 g, 12.97 mM) was hydrolyzed as described in Example 4b to give 2.68 g (quantitative) of a clear gum: tlc, $R_f=0.05$, silica gel, ethyl acetate:hexane (1:3).

c.
5-(1-Oxo-5-(3,3-dichloro-2-propenyl)-2-cyclopenten-3-yl)amino-1-pentyl-4-cyanopyrazole (Formula IV, $R^1=$pentyl, $R^2=R^5=R^6=R^7=H$, $R^4=$3,3-dichloro-2-propenyl, A=a direct link)

A procedure similar to that used in Example 2a was followed except that 2.68 g (12.97 mM) of the ketone produced in Example 30b was reacted with 2.31 g (12.97 mM) of the pyrazole described in Example 1. After an initial work-up like that employed in Example 2a, the material was run over a column of silica gel using ethyl acetate:hexane (1:1) as the eluent; 2.78 g (58%) of a tan solid were obtained: tlc, $R_f=0.10$, ethyl acetate:hexane (1:1).

d.
4-Amino-6-(3,3-dichloro-2-propenyl)-6,7-dihydro-1-pentylcyclopenta[b]pyrazolo[4,3-e]pyridin-5(1H)-one (Formula I, $R^1=$pentyl, $R^2=R^3=R^5=R^6=R^7=H$, $R^4=$3,3-dichloro-2-propenyl, A=a direct link)

A procedure analogous to that described in Example 15d was employed using the product of Example 30c (2.78 g, 7.57 mM) and 1.85 g (15.14 mM) of copper (I) acetate in 12 ml of butyl acetate and 3 ml DMF. After completion of the reaction and work-up, the crude product was passed through a silica gel plug eluting with ethyl acetate:hexane (1:1), followed by recrystallization of the product from tert-butyl methyl ether/hexane. There was obtained 2.20 g (79%) of a white solid; mp, 142°-143° C.; tlc, $R_f=0.21$, silica gel, ethyl acetate:hexane (1:1); MS, m/e 367.

Elemental Analysis: Calculated for $C_{17}H_{20}N_4OCl_2$: C, 55.59; H, 5.49; N, 15.25. Found: C, 55.23: H, 5.46, N, 15.31.

EXAMPLE 31 a. 5-Amino-1-(3-pentynyl)-4-cyanopyrazole (Formula II, $R^1=$3-pentynyl, $R^2=H$)

To a suspension of 5-amino-4-cyanopyrazole (15 g) and finely ground potassium carbonate (58 g) in dry DMF (100 ml) was added 1-bromo-3-pentyne (24.5 g). After stirring at room temperature under nitrogen for 2 days, additional portions of potassium carbonate (10 g) and 1-bromo-3-pentyne (5 g) were added. After three more days of stirring, a final portion of 1-bromo-3-pentyne (5 g) was added, and the reaction allowed to proceed two more days. At this time the reaction mixture was poured into water and the product extracted into ethyl acetate. The extract was washed with brine, dried over $Na_2SO_4$, and evaporated to an oil which was subject to preliminary purification on a column of flash silica gel. Elution with hexane/ethyl acetate (2:1) gave a mixture of the isomeric compounds 5-amino-4-cyano-1-(3-pentynyl)pyrazole and 3-amino-4-cyano-1-(3-pentynyl)pyrazole. This mixture was separated by preparative high pressure liquid chromatography (HPLC) on silica gel, using hexane/ethyl acetate (1:1) as eluent. After pooling appropriate fractions, recrystallization from ethyl acetate/hexane gave 5.05 g of the desired 5-amino-4-cyano-1-(3-pentynyl)pyrazole; mp, 116.5°-117°.

b.
5-(1-Oxo-5-(3,3-dichloro-2-propenyl)-2-cyclopenten-3-yl)amino-1-(3-pentynyl)-4-cyanopyrazole (Formula IV, $R^1=$3-pentynyl, $R^2=R^5=R^6=R^7=H$, $R^4=$3,3-dichloro-2-propenyl, A=a direct link)

The title compound was prepared by heating together 0.45 g (2.58 mM) of the pyrazole produced in Example 31a and 0.64 g (3.09 mM) of the diketone produced in Example 30b in 10 ml of toluene as described in Example 2a. The product obtained was purified over silica gel using ethyl acetate:hexane (2:3) as the eluent. There was obtained 0.64 g (68%) of product: tlc, $R_f=0.39$, silica gel, ethyl acetate (100%).

c.
4-Amino-6-(3,3-dichloro-2-propenyl)-6,7-dihydro-1-(3-pentynyl)cyclopenta[b]pyrazolo[4,3-e]pyridin-5(1H)-one (Formula I, $R^1=$3-pentynyl, $R^2=R^3=R^5R^6=R^7=H$, $R^4=$3,3-dichloro-2-propenyl, A=a direct link)

A procedure analogous to that described in Example 15d was used except the enamine prepared in Example 31b (0.60 g, 1.65 mM) was cyclized with 0.89 g (7.28 mM) of copper (I) acetate in 3 ml n-butyl acetate and 1 ml DMF. Following the work-up the crude product was passed through a silica gel plug using ethyl acetate:hexane (7:13) as the eluent. After recrystallization from tert-butyl methyl ether, the title compound was obtained as 0.049 g (8.1%) of a tan solid; mp, 170°-171.5°: tlc, $R_f=0.27$, silica gel, ethyl acetate:hexane (1:1): MS, m/e 363.

Elemental Analysis: Calculated for $C_{17}H_{16}Cl_2N_4O$: C, 56.21; H, 4.44; N, 15.43. Found: C, 56.06; H, 4.34; N, 15.14.

EXAMPLE 32 a. 5-Amino-4-cyano-1-(2-hydroxyethyl)pyrazole (Formula II, $R^1$=2-hydroxyethyl, $R^2$=H)

A procedure analogous to that described in Example 1 was followed except 20.0 g (164 mM) of ethoxymethylene malononitrile in 250 ml of warm ethanol were added to 13.4 ml (15.0 g, 197 mM) of 2-hydroxyethylhydrazine in 30 ml of ethanol maintained at 45°–50°. Following completion of the reaction and subsequent cooling of the mixture, the crystalline product was removed by filtration, and washed with ether to afford 20.5 g (82%) of the title compound: mp, 160°–161°: tlc, $R_f$=0.28, silica gel, ethyl acetate (100%).

b. 5-Amino-1-(2-chloroethyl)-4-cyanopyrazole (Formula II, $R^1$=2-hydroxyethyl, $R^2$=H)

To a room temperature solution containing 5.0 g (32.9 mM) of the pyrazole described in Example 32a and 10.3 g (39.4 mM) of triphenylphosphine in 50 ml of methylene chloride were added dropwise 16.0 ml (25.4 g, 165 mM) of carbon tetrachloride. The resulting mixture was stirred for about 15 hours at ambient temperature followed by removal of the volatiles. The crude solid was dissolved in THF and purified on a silica gel column using ethyl acetate:hexane (1:1) as the eluent. There were obtained 3.76 g (67%) of a white solid: mp, 157°–158°; tlc, $R_f$=0.27, ethyl acetate:hexane (1:1).

c. 5-(1-Oxo-6-(2-propenyl)-2-cyclohexen-3-yl)amino-1-(2-chloroethyl)-4-cyanopyrazole (Formula IV, $R^1$=2-chloroethyl, $R^2$=$R^5$=$R^6$=$R^7$=$R^8$=$R^9$=H, $R^4$=2-propenyl, n=1)

A mixture of 2.5 g (14.6 mM) of the pyrazole prepared in Example 32b and 2.6 g (17.52 mM) of the diketone prepared in Example 12b were heated together in 25 ml of toluene containing a catalytic amount of para-toluenesulfonic acid as described in Example 2a. Following work-up the crude product was purified by column chromatography using ethyl acetate:hexane (1:1) as the eluent. The title compound was obtained as a thick oil of 4.29 g (96%): tlc, $R_f$=0.23, silica gel, ethyl acetate:hexane (3:1).

d. 4-Amino-1-(2-chloroethyl)-6-(2-propenyl)-5H-1,6,7,8-tetrahydropyrazolo[3,4-b]quinolin-5-one (Formula I, $R^1$=2-chloroethyl, $R^2$=$R^3$=$R^5$=$R^6$=$R^7$=$R^8$=$R^9$=H, $R^4$=2-propenyl, n=1)

To a solution of 4.26 g (14.0 mM) of the enamine prepared in Example 32c in 60 ml of methylene chloride maintained at 0° under an argon atmosphere were added dropwise 21.1 ml of a 1.35M solution (28.5 mM) of trimethylaluminum in n-heptane. Following the addition, the resulting yellow solution was gradually warmed to room temperature and stirred overnight. The solution was gently refluxed for 5.5 hours and then cooled in an ice-bath. 10% Aqueous hydrochloric acid was added cautiously and then the solution was stirred for 30 minutes. Enough 10% aqueous sodium hydroxide was then added to bring the pH to about 10 and the mixture partitioned between ether and the aqueous phase. After further extracting the aqueous phase with ethyl acetate, the combined organic phase was washed with brine, dried over anhydrous $MgSO_4$ and concentrated. The crude product (3.18 g) was recrystallized from tert-butyl methyl ether to leave 2.90 g (68%) of a white crystalline solid: mp, 139°–140°: tlc, $R_f$=0.23, silica gel, ethyl acetate:hexane (1:1): MS, m/e 304.

Elemental Analysis: Calculated for $C_{15}H_{17}N_4ClO$: C, 59.11; H, 5.62; N, 18.38. Found: 58.89; H, 5.58; N, 18.37.

EXAMPLE 33 a. 5-Amino-1-(4-chlorophenyl)-4-cyanopyrazole (Formula II, $R^1$=4-chlorophenyl, $R^2$=H)

A procedure analogous to that described in Example 1 was followed except 3.00 g (24.6 mM) of ethoxymethylene malononitrile were added to 4.39 g (30.8 mM) of 4-chlorophenylhydrazine in 20 ml of ethanol. After completion of the reaction and cooling to ambient temperature, 3.22 g (60%) of the product was obtained as a fluffy tan solid; tlc, $R_f$=0.42, silica gel, ethyl acetate:hexane (1:1).

b. 5-(1-Oxo-2-cyclohexen-3-yl)amino-1-(4-chlorophenyl)-4-cyanopyrazole (Formula IV, $R^1$=4-chlorophenyl, $R^2$=$R^4$=$R^5$=$R^6$=$R^7$=$R^8$=$R^9$=H, n=1)

A procedure analogous to that used in Example 2a was followed using 1.0 g (8.92 mM) of 1,3-cyclohexanedione and 1.50 g (6.86 mM) of the pyrazole produced in Example 33a in 10 ml of toluene. Following completion of the reaction the crude product was isolated as described in Example 2a and purified by column chromatography over silica gel eluting with ethyl acetate:hexane (1:1). There was obtained 1.72 g (80%) of the desired product: tlc, $R_f$=0.09, silica gel, ethyl acetate:hexane (1:1).

c. 4-Amino-1-(4-chlorophenyl)-5H-1,6,7,8-tetrahydropyrazolo-[3,4-b]quinolin-5-one (Formula I, $R^1$=4-chlorophenyl, $R^2$=$R^3$=$R^4$=$R^5$=$R^6$=$R^7$=$R^8$=$R^9$=H, n=1)

The enamine (1.72 g, 5.50 mM) prepared in Example 33b was cyclized according to the procedure of Example 15d using 1.34 g (11.0 mM) of copper (I) acetate in 10 ml of n-butyl acetate and 5 ml of DMF. Following completion of the reaction, the crude product was isolated as described in Example 15d and passed through a short silica gel plug using ethyl acetate:hexane (1:1) as the eluent. After recrystallization from acetonitrile, 0.69 g (40%) of the title compound was obtained as a tan solid; mp, 254°–255°: tlc, $R_f$=0.48, silica gel, ethyl acetate:hexane (1:1); MS, m/e 312.

Elemental Analysis: Calculated for $C_{16}H_{13}N_4ClO$: C, 61.45; H, 4.19; N, 17.91. Found: C, 61.26: H, 4.29: N, 17.85.

EXAMPLE 34 a. 5-Amino-1-benzyl-4-cyanopyrazole (Formula II $R^1$=benzyl, $R^2$=H)

A procedure analogous to that described in Example 1 was followed except 1.55 g (12.7 mM) of ethoxymethylene malononitrile was added to 1.70 g (13.9 mM) of benzylhydrazine in ethanol. Following completion of the reaction 0.82 g (33%) of the product was obtained as a tan solid; tlc, $R_f$=0.24, silica gel, ethyl acetate:hexane (1:1).

b.
5-(1-Oxo-2-cyclohexen-3-yl)amino-1-benzyl-4-cyanopyrazole (Formula IV, $R^1$=benzyl, $R^2=R^4=R^5=R^6=R^7=R^8=R^9$=H, n=1)

A procedure similar to that used in Example 2a was followed using 0.60 g (5.38 mM) of 1,3-cyclohexanedione and 0.82 g (4.14 mM) of the pyrazole prepared in Example 34a in 7 ml of toluene. The crude product was purified by column chromatography using ethyl acetate:hexane (1:1) as the eluent. There was obtained 0.58 g (48%) of a white solid; tlc, $R_f$=0.07, silica gel, ethyl acetate:hexane (1:1).

c.
4-Amino-1-benzyl-5H-1,6,7,8-tetrahydropyrazolo[3,4-b]quinolin-5-one (Formula I, $R^1$=benzyl, $R^2=R^3=R^4=R^5=R^6=R^7=R^8=R^9$=H, n=1)

The enamine (0.58 g, 1.98 mM) prepared in Example 34b was cyclized according to the procedure of Example 15d using 0.48 g (3.97 mM) of copper (I) acetate in 5 ml of n-butyl acetate and 2 ml of DMF. The crude product obtained after work-up was passed through a silica gel plug using ethyl acetate:hexane (1:1) as the eluent. After recrystallization from acetonitrile there was obtained 0.37 g (64%) of the title compound as orange crystals; mp, 213°-214°: tlc, $R_f$=0.20, silica gel, ethyl acetate:hexane (1:1); MS, m/e 292.

Elemental Analysis: Calculated for $C_{19}H_{16}N_4O$: C, 69.85; H, 5.52; N, 19.16. Found: C, 69.48; H, 5.51; N, 19.20.

EXAMPLE 35 a.
4-Amino-1-ethenyl-6-(2-propenyl)-5H-1,6,7,8-tetrahydropyrazolo[3,4-b]quinolin-5-one (Formula I, $R^1$=ethenyl, $R^2=R^3=R^5=R^6=R^7=R^8=R^9$=H, $R^4$=2-propenyl, n=1)

To a room temperature solution of 2.64 g (8.66 mM) of the product described in Example 32d in 10 ml of DMF were added 2.59 ml (2.64 g, 17.62 mM) of 1,8-diazabicyclo[5.4.0]undec-7-ene (DBU). The resulting dark solution was heated to 100° and stirred 3 hours. After cooling to ambient temperature, the mixture was diluted with excess water and the product extracted into ethyl acetate:ether (1:1). The combined organic phase was washed with 10% aqueous acetic acid, then saturated aqueous $Na_2CO_3$ followed by brine. After drying the organic phase over $Na_2SO_4$ and concentrating it, the product was obtained as a crude brown solid. After redissolution in a small amount of THF, the product was purified over silica gel using ethyl acetate/hexane as the eluent. After recrystallization from tert-butyl methyl ether/hexane, 1.96 g (84%) of the title compound was obtained; mp, 141.5°-142.5°; tlc, $R_f$=0.51, silica gel, ethyl acetate: hexane (1:1).

b.
4-Amino-6-(2-propenyl)-5H-1,6,7,8-tetrahydropyrazolo[3,4-b]-quinolin-5-one (Formula I, $R^1=R^2=R^3=R^5=R^6=R^7=R^8=R^9$=H, $R^4$=2-propenyl, n=1)

To a suspension of 1.70 g (6.33 mM) of the product described in Example 35a in 25 ml of acetonitrile were added 10.5 ml of aqueous 6 N hydrochloric acid. The mixture was heated to gentle reflux with stirring for 3.5 hours. After cooling to ambient temperature, water was added, followed by enough saturated aqueous $Na_2CO_3$ to neutralize the pH. The solid was filtered off, washed with water then washed with ether and dried to yield 1.52 g (99%) of the title compound. A sample was recrystallized from ethyl acetate/methanol: mp, 244°-247° (decomposition); tlc, $R_f$=0.21, silica gel, ethyl acetate (100%).

EXAMPLE 36

4-Amino-1-(3-pentynyl)-6-(2-propenyl)-5H-1,6,7,8-tetrahydropyrazolo[3,4-b]quinolin-5-one (Formula I, $R^1$=3-pentynyl, $R^2=R^3=R^5=R^6=R^7=R^8=R^9$=H, $R^4$=2-propenyl, n=1)

To a room temperature mixture of the product prepared in Example 35b (0.70 g, 2.88 mM) and 1.20 g (8.66 mM) of powdered $K_2CO_3$ in 8.0 ml of DMF was added 0.51 g (3.46 mM) of 5-bromo-2-pentyne. The mixture was warmed to 40° and stirred overnight (about 16 hours). At this point an additional equivalent of 5-bromo-2-pentyne (0.42 g, 2.88 mM) was added and the reaction stirred an additional 4 hours. After cooling to ambient temperature, water was added and the aqueous phase extracted three times with ether. The combined extracts were washed with brine, dried over $MgSO_4$ and concentrated to leave a yellow oil. Purification by column chromatography over silica gel eluting with ethyl acetate:hexane (2:3) gave a white solid. Recrystallization from tert-butyl methyl ether afforded 0.50 g (56%) of the title compound: mp, 138.5°-140°; tlc, $R_f$=0.35, silica gel, ethyl acetate:hexane (1:1): MS, m/e 308.

Elemental Analysis: Calculated for $C_{18}H_{20}N_4O$: C, 70.11, H, 6.54; N, 18.17. Found: C, 69.84: H, 6.59; N, 18.12.

EXAMPLE 37

4-Amino-1-(4-pentynyl)-6-(2-propenyl)-5H-1,6,7,8-tetrahydropyrazolo[3,4-b]quinolin-5-one (Formula I, $R^1$=4-pentynyl, $R^2=R^3=R^5=R^6=R^7=R^8=R^9$=H, $R^4$=2-propenyl, n=1)

A procedure similar to that described in Example 36 was employed except 0.77 g (3.18 mM) of the product prepared in Example 35b was reacted with 1.32 g (9.53 mM) of $K_2CO_3$ and 0.75 g (3.82 mM) of 5-iodo-1-pentyne in 10 ml DMF. After stirring 16 hours at 40°, the mixture was cooled to ambient temperature, quenched with water and the product worked-up as described in Example 36. The crude product was purified by column chromatography over silica gel using ethyl acetate:hexane (2:3) as the eluent. After recrystallization from tert-butyl methyl ether, 0.55 g (56%) of the title compound was obtained as a white solid: mp, 118°-119°: tlc, $R_f$=0.34, silica gel, ethyl acetate: hexane (1:1): MS, m/e 308.

Elemental Analysis: Calculated for $C_{18}H_{20}N_4O$: C, 70.11; H, 6.54; N, 18.17. Found: C, 69.95; H, 6.63; N, 18.10.

EXAMPLE 38 a.
5-(1-Oxo-6-(3,3-dichloro-2-propenyl)-2-cyclohexen-3-yl)amino-1-(2-chloroethyl)-4-cyanopyrazole (Formula IV, $R^1$=2-chloroethyl, $R^2=R^5=R^6=R^7=R^8=R^9$=H, $R^4$=3,3-dichloro-2-propenyl, n=1)

A procedure analogous to that detailed in Example 2a was followed except 2.98 g (17.5 mM) of the pyrazole prepared in Example 32b was reacted with 3.67 g (16.6 mM) of the diketone produced in Example 29b in about 20 ml of toluene. Following completion of the reaction and an initial work-up, the crude product was purified by column chromatography over silica gel eluting first with ethyl acetate:hexane:triethylamine (100:100:1) to remove unreacted pyrazole, followed by elution with ethyl acetate: methanol (99:1) to remove the product. There were obtained 4.80 g (80%) of the title compound as a yellow solid; tlc, $R_f$=0.07, silica gel, ethyl acetate:hexane (1:1).

b.
4-Amino-1-(2-chloroethyl)-6-(3,3-dichloro-2-propenyl)-5H-1,6,7,8-tetrahydropyrazolo[3,4-b]quinolin-5-one
(Formula I, $R^1$=2-chloroethyl,
$R^2=R^3=R^5=R^6=R^7=R^8=R^9$=H,
$R^4$=3,3-dichloro-2-propenyl, n=1)

The product prepared in Example 38a (4.80 g, 12.8 mM) in 50 ml of methylene chloride was cyclized according to the procedure described in Example 32d using 20.0 ml (27 mM) of a 1.35 M solution of trimethylaluminum in n-heptane. Following the work-up 4.04 g (84%) of the product was obtained as a yellow solid (crude): tlc, $R_f$=0.19, silica gel, ethyl acetate:hexane (1:1).

c.
4-Amino-6-(3,3-dichloro-2-propenyl)-1-ethenyl-5H-1,6,7,8-tetrahydropyrazolo[3,4-b]quinolin-5-one
(Formula I, $R^1$=ethenyl,
$R^2=R^3=R^5=R^6=R^7=R^8=R^9$=H,
$R^4$=3,3-dichloro-2-propenyl, n=1)

The product described in Example 38b (3.90 g, 10.4 mM) was treated with 3.90 ml (3.97 g, 26.1 mM) of DBU in 30 ml of DMF as described in Example 35a. After heating 3 days at 110°, the reaction was cooled to ambient temperature and the product isolated as described in Example 35a. There was obtained 1.55 g (44%) of the desired product as an amorphous powder; tlc, $R_f$=0.50, silica gel, ethyl acetate:hexane (1:1).

d.
4-Amino-6-(3,3-dichloro-2-propenyl)-5H-1,6,7,8-tetrahydropyrazolo[3,4-b]quinolin-5-one (Formula I,
$R^1=R^2=R^3=R^5=R^6=R^7=R^8=R^9$=H,
$R^4$=3,3-dichloro-2-propenyl, n=1)

The product described in Example 38c (1.55 g, 4.6 mM) was treated with 7.5 ml of aqueous 6 N hydrochloric acid in 15 ml of acetonitrile and 10 ml of DMF as described in Example 35b. After heating for about 24 hours at reflux, the mixture was cooled to ambient temperature and the reaction worked-up as described in Example 35b. There was obtained 1.80 g of a white powder which by $^1$H NMR analysis indicated the presence of 1-2 mole equivalents of water: tlc, $R_f$=0.32, silica gel, ethyl acetate (100%).

EXAMPLE 39

4-Amino-6-(3,3-dichloro-2-propenyl)-1-(4-pentynyl)-5H-1,6,7,8-tetrahydropyrazolo[3,4-b]quinolin-5-one
(Formula I, $R^1$=4-pentynyl,
$R^2=R^3=R^5=R^6=R^7=R^8=R^9$=H,
$R^4$=3,3-dichloro-2-propenyl, n=1)

A procedure analogous to that employed in Example 36 was followed except 0.60 g (1.93 mM) of the product described in Example 38d was reacted with 1.07 g (2.70 mM) of 5-iodo-1-pentyne and 1.07 g (7.71 mM) of powdered $K_2CO_3$ in 10 ml of DMF. After stirring 6 hours at 45°, the mixture was cooled to ambient temperature and the crude product isolated as described in Example 36. After chromatographing the material over silica gel using ethyl acetate:hexane (3:7) as the eluent, there was obtained 0.63 g of a yellow gum. Recrystallization from tert-butyl methyl ether gave 0.38 g (52%) of a white solid: mp, 92.5°–93.5°; tlc, $R_f$=0.30, silica gel, ethyl acetate:hexane (1:1), MS, m/e 377 (M+1, chemical ionization).

Elemental Analysis: Calculated for $C_{18}H_{18}N_4Cl_2O$: C, 57.30: H, 4.81; N, 14.85. Found: C, 57.19; H, 4.92; N, 14.84.

EXAMPLE 40

4-Amino-6-(3,3-dichloro-2-propenyl)-1-(3-pentynyl)-5H-1,6,7,8-tetrahydropyrazolo[3,4-b]quinolin-5-one
(Formula I, $R^1$=3-pentynyl,
$R^2=R^3=R^5=R^6=R^7=R^8=R^9$=H,
$R^4$=3,3-dichloro-2-propenyl, n=1)

The product described in Example 38d (0.81 g, 2.60 mM) was alkylated according to the procedure described in Example 36 except 1.80 g (13.0 mM) of powdered $K_2CO_3$ and two portions of 1-bromo-3-pentyne (each portion being 0.48 g, 3.25 mM) in 10 ml of DMF were used. Following the work-up the resulting orange-brown oil was chromatographed over silica gel using ethyl acetate:hexane (1:1) as the eluent. Recrystallization from tert-butyl methyl ether/hexane gave 0.72 g (74%) of the title compound; mp, 152.5°–153°; tlc, $R_f$=0.63; silica gel, ethyl acetate; MS, m/e 376.

Elemental Analysis: Calculated for $C_{18}H_{18}N_4Cl_2O$: C, 57.30: H, 4.81: N, 14.85. Found: C, 57.50: H, 4.73: N, 14.68.

EXAMPLE 41 a. 6-(2-Butynyl)-3-ethoxy-2-cyclohexenone (Formula IX, $R^4$=2-butynyl, $R^5=R^6=R^7=R^8=R^9$=H, $R^{10}$=ethyl, n=1)

A solution of lithium diisopropylamide was prepared as described in Example 4a using 7.95 ml of a 1.56 M solution (16.4 mM) of n-butyllithium in hexane and 2.30 ml (16.4 mM) of diisopropylamine dissolved in 30 ml of dry THF. The enolate anion of 3-ethoxy-2-cyclohexenone (2.08 ml, 14.3 mM) was then generated from the aforementioned solution of lithium diisopropylamide as described in Example 4a. 1-Bromo-2-butyne (2.28 g, 17.1 mM) was employed as the alkylating agent. HMPA was not used in this example. Following initial work-up, the crude product was purified by column chromatography over silica gel using ethyl acetate:hexane (1:4) as the eluent. There was obtained 2.36 g (86%) of a white solid: tlc, $R_f$=0.31, silica gel, ethyl acetate:hexane (1:3).

b. 4-(2-Butynyl)-1,3-cyclohexanedione (Formula III, $R^4$=2-butynyl, $R^5=R^6=R^7=R^8=R^9$=H, n=1)

The product described in Example 41a (0.70 g, 3.64 mM) was hydrolyzed according to the procedure described in Example 4b except 5ml of 20% aqueous sulfuric acid in 5 ml of THF were used. Following work-up, there was obtained 0.70 g of a thick gum; tlc, $R_f$=0.05, silica gel, ethyl acetate:hexane (1:3).

c.

5-(1-Oxo-6-(2-butynyl)-2-cyclohexen-3-yl)amino-1-pentyl-4-cyanopyrazole (Formula IV, $R^1$=pentyl, $R^2=R^5=R^6=R^7=R^8=R^9$=H, $R^4$=2-butynyl, n=1)

The pyrazole (0.65 g, 3.65 mM) described in Example 1 was heated together with the product prepared in Example 41b (0.60 g, 3.65 mM) and a catalytic amount of para-toluenesulfonic acid in 5 ml of toluene as described in Example 2a. Following completion of the reaction and work-up, the resulting brown oil was purified over silica gel using ethyl acetate:hexane (1:1) as the eluent. There was obtained 1.05 g (89%) of a yellow oil; tlc, $R_f$=0.18, silica gel, ethyl acetate:hexane (1:1).

d.

4-Amino-6-(2-butynyl)-1-pentyl-5H-1,6,7,8-tetrahydropyrazolo-[3,4-b]quinolin-5-one (Formula I, $R^1$=pentyl, $R^2=R^3=R^5=R^6=R^7=R^8=R^9$=H, $R^4$=2-butynyl, n=1)

The enamine (1.05 g, 3.24 mM) described in Example 41c was cyclized using 4.79 ml of a 1.35 M solution (6.47 mM) of trimethylaluminum in n-heptane in 10 ml of $CH_2Cl_2$ according to the procedure of Example 32d. Following the work-up as in Example 32d, the crude product was passed through a silica gel plug eluting with ethyl acetate/hexane. Recrystallization from tert-butyl methyl ether/hexane afforded 0.62 g (59%) of the title compound as white crystals; mp, 128.5°-130°; tlc, $R_f$=0.39, silica gel, ethyl acetate: hexane (1:1); MS, m/e 324.

Elemental Analysis: Calculated for $C_{19}H_{24}N_4O$: C, 70.34; H, 7.46; N, 17.27. Found C, 69.65; H, 7.43; N, 16.87.

EXAMPLE 42 a.

6-(3,3-Dimethyl-2-propenyl)-3-ethoxy-2-cyclohexenone (Formula IX, $R^4$=3,3-dimethyl-2-propenyl, $R^5=R^6=R^7=R^8=R^9$=H, $R^{10}$=ethyl, n=1)

A solution of lithium diisopropylamide was prepared as described in Example 4a using 17.9 ml of a 1.11 M solution (19.9 mM) of n-butyllithium in hexane and 2.79 ml (19.9 mM) of diisopropylamine in 15 ml of THF. The enolate anion derived from 17.3 mM (2.52 ml) of 3-ethoxy-2-cyclohexenone was then generated from the aforementioned solution of lithium diisopropylamide as described in Example 4a. 3,3-Dimethyl-1-bromo-2-propene (7.73 g, 52 mM) was added as the alkylating agent followed by 1.6 ml (9.2 mM) of HMPA as a cosolvent. After aqueous work-up as described in Example 4a there was obtained a crude yellow oil which was purified by column chromatography over silica gel using ethyl acetate:hexane (1:3) as the eluent. The title compound was obtained as 1.42 g (39%): tlc, $R_f$=0.54, silica gel, ethyl acetate:hexane (2:3).

b. 4-(3,3-Dimethyl-2-propenyl)-1,3-cyclohexanedione (Formula III, $R^4$=3,3-dimethyl-2-propenyl, $R^5R^6R^7R^8R^9$=H, n=1)

The product prepared in Example 42a (1.42 g, 6.81 mM) was hydrolyzed according to the procedure described in Example 4b using 22 ml of aqueous 10% hydrochloric acid in 7 ml of THF. After work-up there was obtained 1.14 g (93%) of the desired product: tlc, $R_f$=0.18, silica gel, ethyl acetate:hexane (2:3).

c.

5-(1-Oxo-6-(3,3-dimethyl-2-propenyl)-2-cyclohexen-3-yl)amino-1-pentyl-4-cyanopyrazole (Formula IV, $R^1$=pentyl, $R^2=R^5=R^6=R^7=R^8=R^9$=H, $R^4$=3,3-dimethyl-2-propenyl, n=1)

The title compound was prepared as described in Example 2a except that 1.14 g (6.3 mM) of the diketone produced in Example 42b was reacted with 0.99 g (5.58 mM) of the pyrazole described in Example 1. Following work-up, the product was purified with silica gel chromatography using ethyl acetate: hexane (2:3) as the eluent. There was obtained 1.07 g (58%) of the desired product; tlc, $R_f$=0.38, silica gel, ethyl acetate: hexane (1:1).

d.

4-Amino-6-(3,3-dimethyl)-2-propenyl)-1-pentyl-5H-1,6,7,8-tetrahydropyrazolo[3,4-b]quinolin-5-one (Formula I, $R^1$=pentyl, $R^2=R^3=R^5=R^6=R^7=R^8=R^9$=H, $R^4$=3,3-dimethyl-2-propenyl, n=1)

The enamine (1.04 g, 3.06 mM) described in Example 42c was cyclized according to the procedure of Example 32d using 4.54 ml of a 1.35 M solution (6.13 mM) of trimethylaluminum in n-heptane in 10 ml of methylene chloride. Following the work-up, there was obtained 1.30 g of a crude solid. After dissolving in THF, the material was chromatographed over silica gel using ethyl acetate:hexane (1:1) as the eluent. Recrystallization from tert-butyl methyl ether gave 0.70 g (67%) of the title compound; mp, 114.5-115.50°; tlc, $R_f$=0.63, silica gel, ethyl acetate:hexane (1:1): MS, m/e 340.

Elemental Analysis: Calculated for $C_{20}H_{28}N_4O$: C, 70.56; H, 8.29; N, 16.46. Found: C, 70.61; H, 8.32; N, 16.61.

EXAMPLE 43 a.

5-(1-Oxo-5-(2-propenyl)-2-cyclopenten-3-yl)amino-1-(3-pentynyl)-4-cyanopyrazole (Formula IV, $R^1$=3-pentynyl, $R^2=R^5=R^6=R^7$=H, $R^4$=2-propenyl, A=a direct link)

A mixture of 1.38 g (7.92 mM) of the pyrazole described in Example 31a, 1.42 g (10.3 mM) of the diketone described in Example 15a and a catalytic amount of para-toluenesulfonic acid were heated together in 10 ml of toluene according to the procedure of Example 2a. Following completion of the reaction the crude product was isolated as also described in Example 2a and subsequently purified by column chromatography over silica gel using ethyl acetate:hexane (1:1) as the eluent. The chromatographed material was recrystallized from tert-butylmethyl ether to give 1.59 g (68%) of the title compound as a white solid; tlc, $R_f$=0.33, silica gel, ethyl acetate (100%).

b.

4-Amino-6-(2-propenyl)-6,7-dihydro-1-(3-pentynyl)cyclopenta-[b]pyrazolo[4,3-e]pyridin-5(1H)-one (Formula I, $R^1$=3-pentynyl, $R^2=R^3=R^5=R^6=R^7$=H, $R^4$=2-propenyl, A=a direct link)

A suspension of 0.20 g (4.64 mM) of NaH (55% in oil) was stirred with 15 ml of dry THF for several minutes. The sodium hydride was allowed to settle with the THF supernatant removed by decanting away. After resuspending the sodium hydride in 5 ml of THF and cooling to 0°, a solution of 1.30 g (4.42 mM) of the product described in Example 43a in 3 ml of THF was added slowly. Following the addition, the solution was warmed slowly to ambient temperature, stirring 30 minutes. Solid, dry cadmium chloride (1.01 g, 5.53 mM) was added all at once followed by 1.0 ml of dry DMF. The mixture was then gradually warmed to ca. 90° (bath temperature) and maintained at that temperature for 15 minutes. To the mixture was added slowly 5.0 ml of toluene with the temperature increased to 110°. The reaction was stirred six hours at 110° followed by cooling to ambient temperature and diluting with 25 ml of ethyl acetate. To this was slowly added enough saturated aqueous ethylenediamine tetracetic acid disodium salt to give a final pH of about 4. The layers were separated with the aqueous phase further extracted twice with equal volumes of ethyl acetate. The combined organic phase was washed sequentially with saturated aqueous sodium bicarbonate then brine followed by drying over sodium sulfate. After concentration the crude product was purified by column chromatography over silica gel using ethyl acetate:hexane (2:3) as the eluent. The purified material was recrystallized from ethyl acetate/hexane to give 1.01 g (79%) of the title compound as a white solid; mp, 169.5–170°, tlc, $R_f$=0.28, silica gel, ethyl acetate:hexane (1:1).

What is claimed is:

1. A compound of formula I as follows:

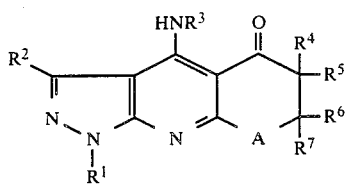

wherein

A is a direct link; or a divalent radical having the formula $(CR^8R^9)_n$;

n=1 or 2;

$R^1$ is hydrogen; an alkyl of 1 to 10 carbons optionally substituted independently by a member selected from a group consisting of hydroxy, cyano, oxo and alkoxy having 1 to 6 carbons, or by one to three member(s) selected from a group consisting of halogen, an alkyl having 1 to 6 carbons, and a halogenoalkyl substituted by 1 to 3 halogens; a cycloalkyl of 3 to 8 carbons; a cycloalkylalkyl of 4 to 12 carbons; an alkenyl or alkynyl of 2 to 10 carbons, optionally substituted independently by 1 to 3 member(s) selected from a group consisting of halogen and an alkyl of 1 to 6 carbons; an aryl of 6 to 10 carbons optionally substituted independently by one or two member(s) selected from a group consisting of halogen, hydroxy, an alkyl of 1 to 6 carbons, an alkyl of 1 to 6 carbons substituted by one or more fluoros, and an alkoxy of 1 to 6 carbons; an arylalkyl having 6 to 10 carbons in the aryl and 1 to 4 carbons in the alkyl, wherein said aryl portion may optionally be substituted independently by 1 or 2 member(s) selected from a group consisting of halogen, hydroxy, an alkyl of 1 to 6 carbons, an alkyl of 1 to 6 carbons substituted by one or more fluoros, and an alkoxy of 1 to 6 carbons;

$R^2$ is hydrogen; or an alkyl of 1 to 6 carbons;

$R^3$ is hydrogen; an alkyl of 1 to 6 carbons optionally substituted by a member selected from a group consisting of hydroxy and oxo; an alkanoyl of 2 to 6 carbons; or an aroyl of 6 to 10 carbons;

$R^4$ and $R^5$, may be the same or different and are each hydrogen; an alkyl of 1 to 10 carbons optionally substituted independently by one or two member(s) selected from a group consisting of hydroxy, oxo, alkoxy of 1 to 6 carbons, an alkyl of 1 to 6 carbons, and a halogenoalkyl having 1 to 6 carbons and 1 to 3 halogens; a cycloalkyl of 3 to 8 carbons; a cycloalkylalkyl of 4 to 10 carbons; an alkenyl or alkynyl of 3 to 10 carbons optionally substituted independently by 1 to 3 member(s) selected from a group consisting of an alkyl of 1 to 6 carbons and halogen; a cycloalkenyl of 4 to 8 carbons optionally substituted independently by 1 or 2 member(s) selected from a group consisting of halogen and an alkyl having 1 to 6 carbons; a cycloalkenylalkyl wherein the cycloalkenyl portion has 4 to 8 carbons and the alkyl portion has 1 to 3 carbons, optionally substituted independently in the cycloalkenyl portion by 1 or 2 member(s) selected from a group consisting of an alkyl of 1 to 6 carbons; an aryl of 6 to 10 carbons optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, amino and a halogenoalkyl having 1 to 6 carbons and 1 to 3 of halogen; an arylalkyl having 6 to 10 carbons in the aryl portion and 1 to 4 carbons in the alkyl wherein the aryl portion is optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, an amino and a halogenoalkyl having 1 to 6 carbons and 1 to 3 of halogen; an alkanoyl of 1 to 6 carbons; or an aryl (oxo-substituted)alkyl of 7 to 12 carbons; or, when taken together with the carbon atom to which they are attached, $R^4$ and $R^5$ may be selected to form a spiro ring having from 4 to 7 carbons wherein said spiro ring may optionally be substituted by a member selected from a group consisting of an alkyl having 1 to 6 carbons and an alkenyl having 2 to 6 carbons;

$R^6$, $R^7$, $R^8$ and $R^9$ may be the same or different and are each hydrogen; an alkyl of 1 to 6 carbons; or an alkenyl of 2 to 6 carbons;

and a pharmaceutically acceptable salt thereof.

2. A compound according to claim 1 wherein $R^1$ is hydrogen; an alkyl of 2 to 7 carbons optionally substituted by a member selected from a group consisting of hydroxy, oxo, and an alkyl of 1 to 6 carbons, wherein said alkyl of 1 to 6 carbons is optionally substituted by 1 to 3 of chloro or fluoro; a cycloalkyl of 4 to 8 carbons; a cycloalkylalkyl of 4 to 12 carbons; an alkenyl or alkynyl of 2 to 7 carbons optionally substituted independently by 1 to 3 member(s) of a group consisting of halogen and an alkyl of 1 to 6 carbons; an aryl of 6 to 10 carbons optionally substituted independently by one or two member(s) selected from a group consisting of halogen, hydroxy, an alkyl of 1 to 6 carbons, and a fluoroalkyl of 1 to 6 carbons substituted by one or more fluoro; or an arylalkyl having 6 to 10 carbons in the aryl and 1 to 4 carbons in the alkyl, wherein said aryl portion may optionally be substituted by 1 or 2 member(s) selected from a group consisting of halogen, hydroxy, an alkyl of 1 to 6 carbons, a fluoroalkyl of 1 to 6 carbons substituted by one or more of fluoro and an alkoxy of 1 to 6 carbons;

$R^3$ is hydrogen; an alkyl of 1 to 6 carbons optionally substituted by an hydroxy or oxo; an alkanoyl of 2 to 4 carbons; or a benzoyl;

$R^4$ and $R^5$ are the same or different and are each hydrogen; an alkyl of 1 to 6 carbons optionally substituted by a member selected from the group consisting of hydroxy, oxo, an alkoxy of 1 to 6 carbons, an alkyl of 1 to 6 carbons, and a halogenoalkyl having 1 to 6 carbons and 1 to 3 halogens; a cycloalkyl of 4 to 8 carbons; a cycloalkylalkyl of 4 to 10 carbons; an alkenyl or alkynyl of 3 to 6 carbons optionally substituted independently by 1 to 3 member(s) selected from a group consisting of halogen and an alkyl of 1 to 6 carbons; a cycloalkenyl of 4 to 8 carbons optionally substituted independently by 1 or 2 member(s) selected from a group consisting of halogen and an alkyl having 1 to 6 carbons; a cycloalkenylalkyl wherein the cycloalkenyl portion has 4 to 8 carbons and the alkyl portion has 1 to 3 carbons, optionally substituted independently in the cycloalkenyl portion by 1 or 2 member(s) of a group consisting of an alkyl of 1 to 6 carbons; an aryl of 6 to 10 carbons optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, amino and a halogenoalkyl having 1 to 6 carbons and 1 to 3 of halogen; or an arylalkyl having 6 to 10 carbons in the aryl portion and 1 to 4 carbons in the alkyl portion wherein the aryl portion is optionally substituted independently by a member selected from a group consisting of a cyano, an alkoxy carbonyl of 2 to 7 carbons, amino, a mono or dialkyl-substituted amino of 1 to 4 carbons in each alkyl, or by one or two member(s) of a group consisting of halogen, hydroxy, an alkyl of 1 to 6 carbons, an alkanoyl of 1 to 6 carbons, an alkoxy of 1 to 6 carbons, a halogenoalkyl having 1 to 3 of halogen and 1 to 6 carbons, and an alkanoyl of 1 to 6 carbons; or when taken together with the carbon to which they are attached, $R^4$ and $R^5$ may be selected to form a spiro ring which has from 4 to 6 carbons, and which may optionally be substituted by a member selected from a group consisting of an alkyl having 1 to 6 carbons and an alkenyl having 2 to 6 carbons.

3. A compound according to claim 2 wherein $R^1$ is an alkyl of 2 to 7 carbons optionally substituted independently by a member selected from a group consisting of hydroxy, oxo, chloro or by 1 to 3 of fluoro; a cycloalkyl of 4 to 8 carbons; a cycloalkylalkyl of 4 to 10 carbons; alkenyl or alkynyl of 2 to 7 carbons optionally substituted by a member selected from a group consisting of an alkyl of 1 to 4 carbons and a halogen; phenyl; phenyl substituted independently by 1 or 2 member(s) selected from a group consisting of halogen, hydroxy, an alkyl of 1 to 4 carbons, trifluoromethyl and methoxy; benzyl; or (substituted phenyl)alkyl wherein the alkyl portion is 1 to 4 carbons and the substitution is 1 or 2 member(s) selected from a group consisting of halogen, hydroxy, an alkyl of 1 to 4 carbons, trifluoromethyl and methoxy;

$R^2$ is hydrogen;

$R^3$ is hydrogen; an alkyl of 1 to 4 carbons optionally substituted by hydroxy or oxo; acetyl; propanoyl; butanoyl; or benzoyl;

$R^4$ and $R^5$ are the same or different and are each hydrogen; an alkyl of 1 to 6 carbons optionally substituted by a member selected from a group consisting of hydroxy, oxo, an alkyl of 1 to 4 carbons and a halogenoalkyl of 1 to 4 carbons having 1 to 3 of halogen; a cycloalkyl of 4 to 8 carbons; an alkenyl or alkynyl of 3 to 6 carbons optionally substituted independently by 1 to 3 member(s) of a group consisting of halogen and an alkyl of 1 to 4 carbons; a cycloalkenyl of 5 to 8 carbons; an aryl of 6 to 10 carbons; a phenyl independently substituted by a member selected from a group consisting of nitro, cyano, an alkoxycarbonyl of 2 to 7 carbons, amino, a mono- or dialkyl-substituted amino of 1 to 4 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, and halogenoalkyl having a halogen and 1 to 6 carbons; a phenyl alkyl having 1 to 4 carbons in the alkyl; (substituted phenyl)alkyl having 1 to 4 carbons in the alkyl wherein the substitution on the phenyl is a member selected from a group consisting of nitro, cyano, alkoxycarbonyl of 2 to 7 carbons, amino, mono- or dialkyl-substituted amino of 1 to 4 carbons in each alkyl, or one or two of halogen, hydroxy, alkyl of 1 to 4 carbons, alkoxy of 1 to 4 carbons, halogenoalkyl of 1 to 4 carbons and 1 to 3 of halogen; benzoyl; or phenylacetyl;

$R^6$, $R^7$, $R^8$ and $R^9$ may be the same or different and are each hydrogen; an alkyl of 1 to 4 carbons; 2-propenyl; or 3-butenyl.

4. A compound according to claim 3 wherein $R^1$ is a straight chain alkyl of 2 to 7 carbons optionally substituted independently by a member selected from a group consisting of hydroxy and chloro or by 1 to 3 of fluoro; an alkenyl or alkynyl of 3 to 6 carbons optionally substituted by an alkyl of 1 to 4 carbons; phenyl; phenyl substituted independently by a member of a group consisting of hydroxy and an alkyl of 1 to 4 carbons, or by 1 or 2 of chloro or fluoro; or a benzyl optionally substituted by a member of a group consisting of chloro, fluoro and an alkyl of 1 to 4 carbons;

$R^3$ is H;

$R^4$ and $R^5$ are the same or different and are each hydrogen; an alkyl of 1 to 6 carbons optionally substituted by a halogenoalkyl of 1 to 4 carbons having 1 to 3 of chloro or fluoro; an alkenyl or alkynyl of 3 to 6 carbons optionally substituted by an alkyl of 1 to 3 carbons or by 1 to 3 of halogen; a phenyl optionally substituted by a chloro, fluoro, hydroxy or an alkyl of 1 to 4 carbons;

R[6], R[7], R[8], R[9] may be the same or different and are each hydrogen; methyl; ethyl; propyl; butyl; 2-propenyl; or 3-butenyl.

5. A compound according to claim 4 wherein

R[1] is a straight chain alkyl of 2 to 5 carbons optionally substituted by a chloro or fluoro; an alkenyl or alkynyl of 3 to 6 carbons wherein a double or triple bond is terminal or one carbon removed from the terminal carbon of said alkenyl or alkynyl; phenyl; or phenyl substituted by a chloro or fluoro;

R[4] and R[5] are the same or different and are each hydrogen; an alkyl of 1 to 5 carbons optionally substituted by a member of a group consisting of chloro and an alkyl of 1 to 2 carbons; an alkenyl or alkynyl of 3 to 6 carbons wherein a double or triple bond is terminal or one carbon removed from the terminal carbon of said alkenyl or alkynyl, and wherein said alkenyl or alkynyl is optionally substituted by 1 or 2 member(s) selected from a group consisting of chloro and methyl; phenyl; or a phenyl substituted by a chloro or fluoro.

6. A compound according to claim 1 selected from the following group:

(a) 4-amino-1-pentyl-6-(2-propenyl)-5H-1,6,7,8-tetrahydropyrazolo[3,4-b]quinolin-5-one;

(b) 4-amino-6,7-dihydro-1-pentyl-6-propylcyclopenta[b]pyrazolo[4,3-e]pyridin-5(1H)-one;

(c) 4-amino-6,7-dihydro-1-pentyl-6-(2-propenyl)cyclopenta[b]pyrazolo[4,3-e]pyridin-5(1H)-one;

(e) 4-amino-6,7-dihydro-1-(4-pentynyl)-6-(2-propenyl)-cyclopenta[b]pyrazolo[4,3-e]pyridin-5(1H)-one;

(f) 4-amino-1-(3-pentynyl)-6-(2-propenyl)-5H-1,6,7,8-tetrahydroapyrazolo[3,4-b]quinolin-5-one;

(g) 4-amino-1-(4-pentynyl)-6-(2-propenyl)-5H-1,6,7,8-tetrahydropyrazolo[3,4-b]quinolin-5-one; and (h) 4-amino-6-(3,3-dichloro-2-propenyl)-1-(4-pentynyl)-5H-1,6,7,8-tetrahydropyrazolo[3,4-b]quinolin-5-one; and pharmaceutically-acceptable acid addition salts thereof.

7. A process for producing a compound as claimed in claim 1 comprising:

(a) for those compounds in which R[3] is hydrogen, internally cyclizing a compound of the following formula IV:

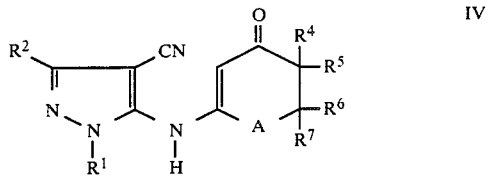

(b) for those compounds in which R[3] is defined as in claim 1 but is other than hydrogen, reacting a compound of formula I in which R[3] is hydrogen with a halide of formula R[13]X in which R[13] has the value for R[3] given in claim 1, excluding hydrogen, and X is a halogen.

8. The process of claim 7 in which said compound of formula IV is heated to a temperature of between 25° C. and 180° C. in the presence of a member selected from a group consisting of $ZnCl_2$, $ZnBr_2$, $CdCl_2$, $CH_3CO_2Cu$, $(CH_3)_3Al$, $(CH_3CH_2)_3Al$ and $(CH_3)_2CHCH_2)_3Al$.

9. The process of claim 7 further comprising forming a pharmaceutically acceptable salt by selecting a compound of formula I in the form of a free base; and reacting said free base with an acid.

10. A compound of formula IV:

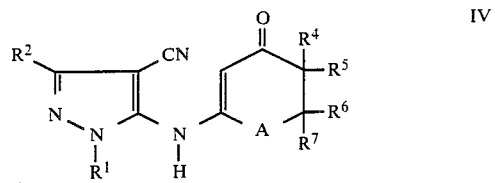

wherein

A is a direct link; or a divalent radical having the formula $(CR^8R^9)_n$;

n=1 or 2;

R[1] is hydrogen; an alkyl of 1 to 10 carbons optionally substituted independently by a member selected from a group consisting of hydroxy, cyano, oxo and alkoxy having 1 to 6 carbons, or by one to three member(s) selected from a group consisting of halogen, an alkyl having 1 to 6 carbons, and a halo-genoalkyl substituted by 1 to 3 halogens; a cycloalkyl of 3 to 8 carbons; a cycloalkylalkyl of 4 to 12 carbons; an alkenyl or alkynyl of 2 to 10 carbons, optionally substituted independently by 1 to 3 member(s) selected from a group consisting of halogen and an alkyl of 1 to 6 carbons; an aryl of 6 to 10 carbons optionally substituted independently by one or two member(s) selected from a group consisting of halogen, hydroxy, an alkyl of 1 to 6 carbons, an alkyl of 1 to 6 carbons substituted by one or more fluoros, and an alkoxy of 1 to 6 carbons; an arylalkyl having 6 to 10 carbons in the aryl and 1 to 4 carbons in the alkyl, wherein said aryl portion may optionally be substituted independently by 1 or 2 member(s) selected from a group consisting of halogen, hydroxy, an alkyl of 1 to 6 carbons, an alkyl of 1 to 6 carbons substituted by one or more fluoros, and an alkoxy of 1 to 6 carbons;

R[2] is hydrogen; or an alkyl of 1 to 6 carbons;

R[4] and R[5], may be the same or different and are each hydrogen; an alkyl of 1 to 10 carbons optionally substituted independently by one or two member(s) selected from a group consisting of hydroxy, oxo, alkoxy of 1 to 6 carbons, an alkyl of 1 to 6 carbons, and a halogenoalkyl having 1 to 6 carbons and 1 to 3 halogens; a cycloalkyl of 3 to 8 carbons; a cycloalkylalkyl of 4 to 10 carbons; an alkenyl or alkynyl of 3 to 10 carbons optionally substituted independently by 1 to 3 member(s) selected from a group consisting of an alkyl of 1 to 6 carbons and halogen; a cycloalkenyl of 4 to 8 carbons optionally substituted independently by 1 or 2 member(s) selected from a group consisting of halogen and an alkyl having 1 to 6 carbons; a cycloalkenylalkyl wherein the cycloalkenyl portion has 4 to 8 carbons and the alkyl portion has 1 to 3 carbons, optionally substituted independently in the cycloalkenyl portion by 1 or 2 member(s) selected from a group consisting of an alkyl of 1 to 6 carbons; an aryl of 6 to 10 carbons optionally substituted independently by a member selected from a group consisting of nitro, cyano, an alkoxycarbonyl of 2 to 7 carbons, and a mono or dialkyl-substituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, amino and a halogenoalkyl having 1 to 6 carbons and 1 to 3 of halogen; an arylalkyl having 6 to 10 carbons in the aryl portion and 1 to 4 carbons in the alkyl wherein the aryl portion is optionally substituted independently by a member selected from a group consisting of nitro, cyano, an alkoxycarbonyl of 2 to 7 carbons, and a mono or dialkylsubstituted amino of 1 to 6 carbons in each alkyl, or by 1 or 2 member(s) selected from a group consisting of halogen, hydroxy, an alkyl of 1 to 6 carbons, an alkanoyl of 1 to 6 carbons, an alkoxy of 1 to 6 carbons, an amino and a halogenoalkyl having 1 to 6 carbons and 1 to 3 of halogen; an alkanoyl of 1 to 6 carbons; or an aryl (oxo-substituted)alkyl of 7 to 12 carbons; or, when taken together with the carbon atom to which they are attached, $R^4$ and $R^5$ may be selected to form a spiro ring having from 4 to 7 carbons wherein said spiro ring may optionally be substituted by a member selected from a group consisting of an alkyl having 1 to 6 carbons and an alkenyl having 2 to 6 carbons;

$R^6$, $R^7$, $R^8$ and $R^9$ may be the same or different and are each hydrogen; an alkyl of 1 to 6 carbons; or an alkenyl of 2 to 6 carbons.

11. A pharmaceutical composition comprising a compound of claim 1 in an amount sufficient to affect anxiolytic activity in a warm blooded animal in association with a non-toxic pharmaceutically-acceptable diluent or carrier.

12. A method of treating anxiety in a living animal comprising administering to the animal a composition of claim 1.

* * * * *